(12) United States Patent
Ichigo et al.

(10) Patent No.: US 8,266,966 B2
(45) Date of Patent: Sep. 18, 2012

(54) ULTRASONIC EXPLORATION METHOD AND ULTRASONIC EXPLORATION APPARATUS

(75) Inventors: Kazuyoshi Ichigo, Aichi (JP); Koichiro Kawashima, Aichi (JP)

(73) Assignee: Central Motor Wheel Co., Ltd., Aichi (JP)

( * ) Notice: Subject to any disclaimer, the term of this patent is extended or adjusted under 35 U.S.C. 154(b) by 379 days.

(21) Appl. No.: 12/726,883

(22) Filed: Mar. 18, 2010

(65) Prior Publication Data
US 2010/0246326 A1    Sep. 30, 2010

(30) Foreign Application Priority Data
Mar. 30, 2009 (JP) ................................. 2009-081304

(51) Int. Cl.
*G01N 29/26* (2006.01)
*G01S 15/00* (2006.01)

(52) U.S. Cl. ............ 73/606; 73/596; 73/610; 73/626; 367/7; 367/93

(58) Field of Classification Search .............. 73/606, 73/596, 610, 626; 600/443, 447; 367/7, 367/93
See application file for complete search history.

(56) References Cited

U.S. PATENT DOCUMENTS

| | | | |
|---|---|---|---|
| 3,156,110 A * | 11/1964 | Clynes ........................ 73/628 |
| 4,322,974 A * | 4/1982 | Abele et al. .................. 73/602 |
| 6,048,316 A * | 4/2000 | Zhao et al. .................. 600/447 |
| 6,371,914 B1 * | 4/2002 | Arditi .......................... 600/443 |
| 6,468,217 B1 * | 10/2002 | Fazioli ........................ 600/443 |
| 6,638,224 B2 * | 10/2003 | Ohtsuki et al. .............. 600/443 |
| 6,816,166 B2 * | 11/2004 | Shimizu et al. ............. 345/581 |

FOREIGN PATENT DOCUMENTS
JP    2007-101329 A    4/2007

* cited by examiner

*Primary Examiner* — J M Saint Surin
(74) *Attorney, Agent, or Firm* — McDermott Will & Emery LLP

(57) ABSTRACT

An exploration operation, in which the transmission/reception position, at which ultrasonic waves are transmitted and received, is changed by a specified pitch distance, is performed for each of a plurality of incident angles. A nonlinear image in which echo signals acquired from harmonic waves of reflected waves are presented is generated for each incident angle. Each nonlinear image is converted into a frame conversion image in accordance with the cross-sectional shape of an exploration-target area. A signal intensity threshold for removing echo signals resulting from an orientation defect is determined in advance. Frame conversion images formed by only echo signals 41a whose signal intensity is the signal intensity threshold or more are overlapped to generate a nonlinear exploration image 35. Exploration of a welded portion 23 stably provides a nonlinear exploration image 35 in which the shape of an interface 25 of the welded portion 23 is shown accurately and clearly.

4 Claims, 9 Drawing Sheets

FIG.3
(A) 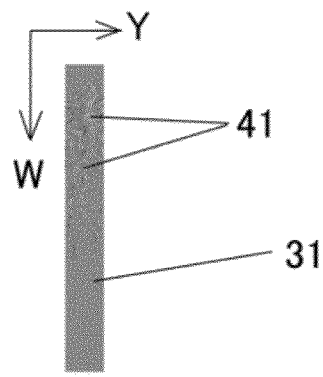
(B) 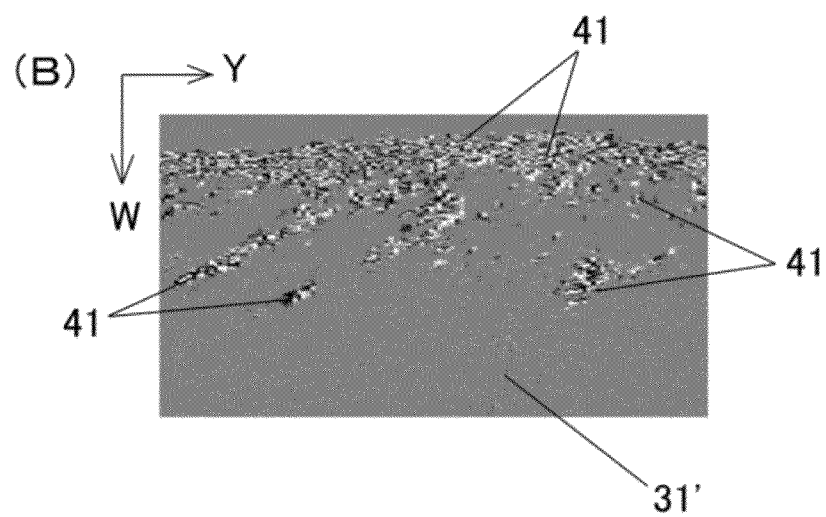
(C) 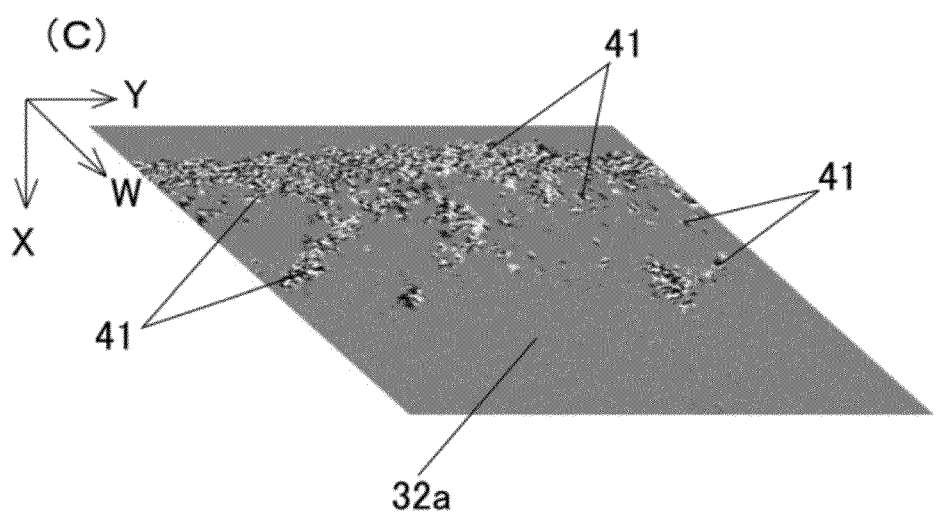

FIG.5
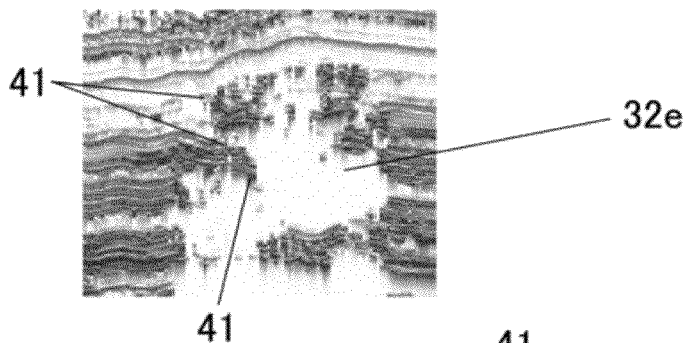
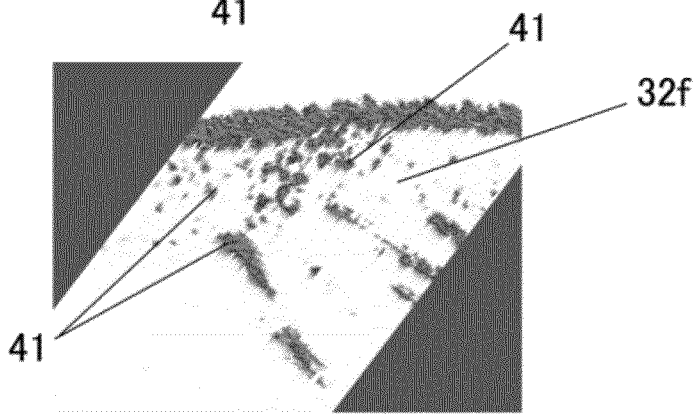
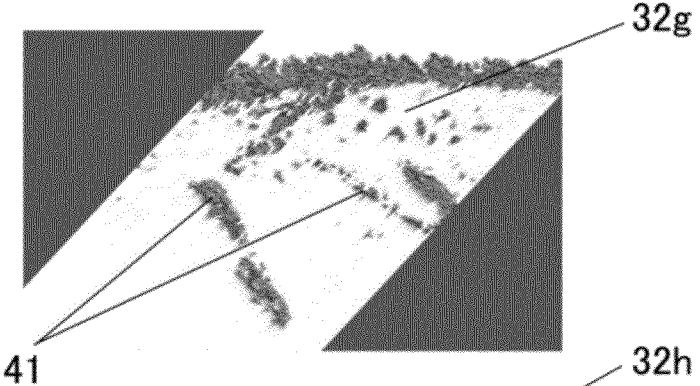
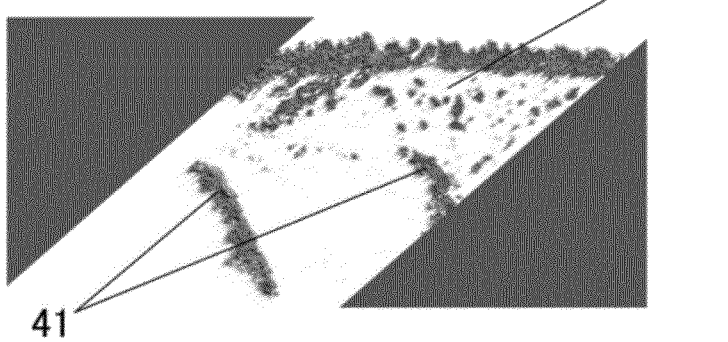

FIG.6
(A)
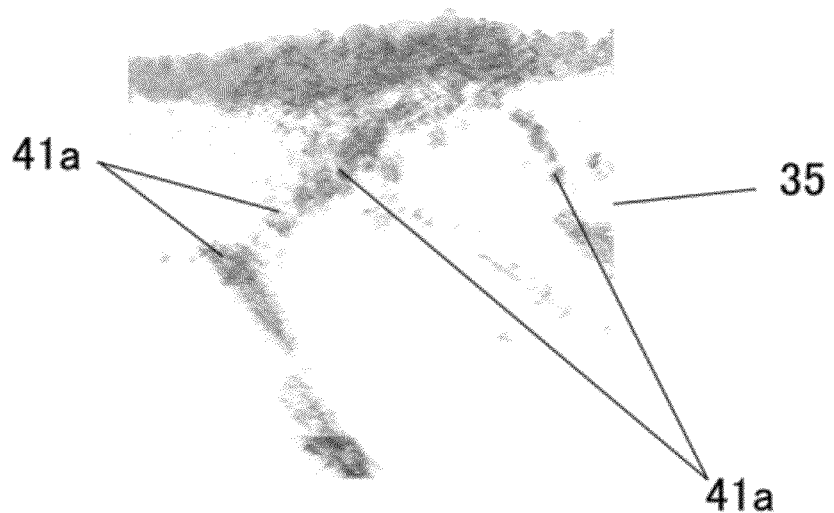
(B)
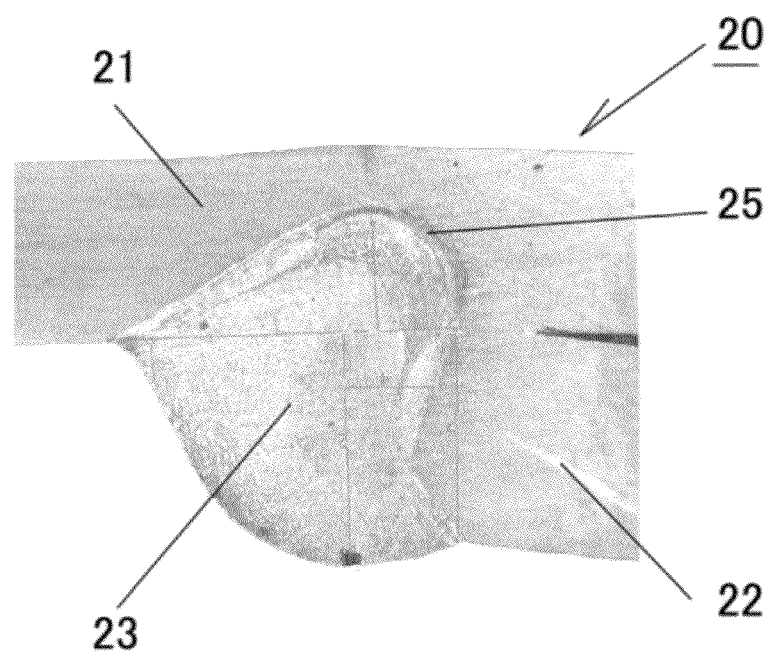

FIG.9
(A)
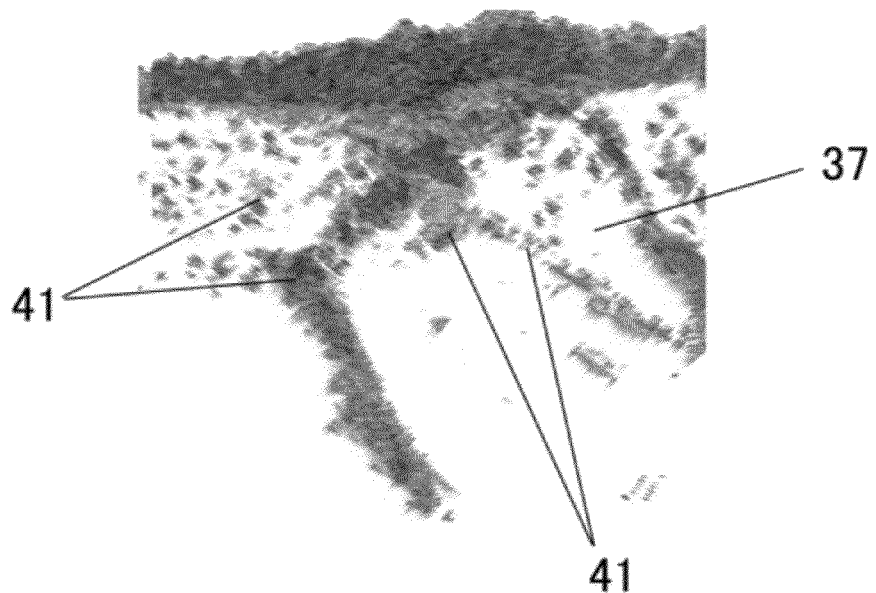
(B)
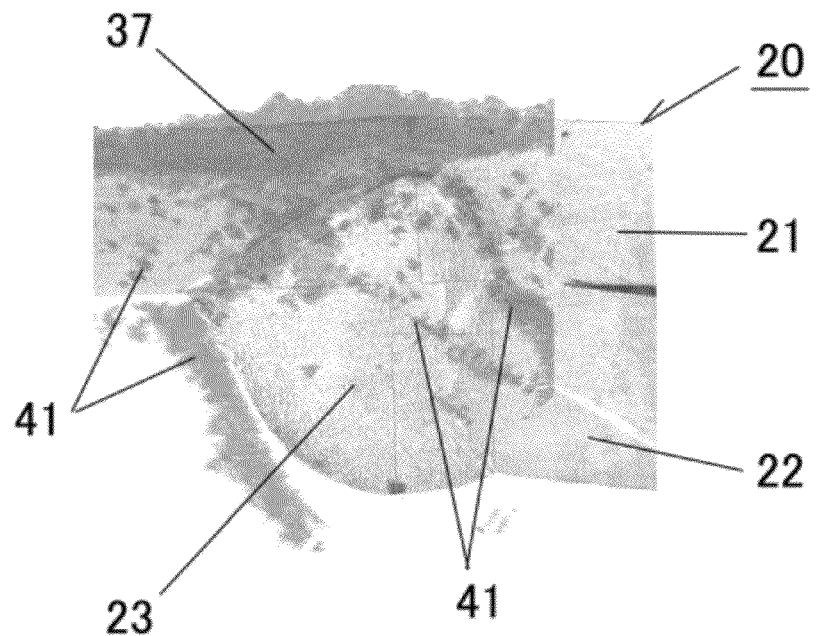

ULTRASONIC EXPLORATION METHOD AND ULTRASONIC EXPLORATION APPARATUS

CROSS-REFERENCE TO PRIOR APPLICATIONS

Priority is claimed to Japanese Patent Application No.2009-081304, filed on Mar. 30, 2009, which is hereby incorporated by reference in its entirety herein.

FIELD OF THE INVENTION

The present invention relates to an ultrasonic exploration method and an ultrasonic exploration apparatus that allow non-destructive exploration of an exploration-target metal body formed by, for example, welding metal members to provide an exploration image of a cross-sectional shape of the exploration-target metal body.

BACKGROUND

Automobile wheels made of steel, for example, typically have a so-called two-piece structure in which a wheel rim and a wheel disc are welded to each other. It is known that the peripheral edge of a flange portion of the wheel disc and the inner circumferential surface of the wheel rim can be joined with each other by fillet welding. Since the automobile wheels are important safety components, it is desired that the automobile wheels fully exhibit their dynamic properties such as specified strength and durability. It is possible to determine whether or not the wheel rim and the wheel disc are joined with each other with an adequate joining strength by investigating the welding depth into the wheel rim and the wheel disc at a welded portion between the wheel rim and the wheel disc.

In order to examine the welding depth at the welded portion in a manufacturing site of the automobile wheels described above, a sampling inspection is normally performed in which an automobile wheel is cut at the welded portion to measure the actual welding depth at the cut surface. In this method, however, the automobile wheel used in the inspection is discarded to increase the production cost in accordance with the proportion of samples. In addition, this method requires various work to be performed sequentially, such as cutting an automobile wheel, polishing the cut surface, and measuring the actual welding depth, which require a relatively large amount of time and effort.

The present inventors propose a non-destructive inspection method that uses ultrasonic waves to inspect a welded portion as described in Japanese Unexamined Patent Publication No. JP2007-101329. In such a method, ultrasonic waves are transmitted to a welded portion and reflected waves are received to extract second-order harmonic waves, and interface-reflected waves reflected by the interface of the welded portion are found out from the second-order harmonic waves to measure the interface depth of the welded portion. According to this method, the interface depth of the welded portion can be measured accurately to allow non-destructive inspection in order to find the greatest welding depth at the welded portion. Further, the interface depth of the welded portion can be measured at each measurement position by changing the measurement position at which ultrasonic waves are transmitted and reflected waves are received to make it possible to know the interface shape of the welded portion on the basis of each interface depth measurement value.

SUMMARY OF THE INVENTION

Problem to be Solved by the Invention

Among inspection methods for a welded portion of a product (for example, an automobile wheel), inspection methods in which a welded portion is cut and actually measured provide a cross-sectional image obtained by photographing the cross-sectional shape (the shape of the cut surface) of the welded portion, and therefore the inspection results of such methods are highly useful. This is because the cross-sectional image (photograph) mentioned above allows immediate understanding of the welding shape of the welded portion, and the welding shape also allows determination as to whether or not the welding is performed adequately. For this reason, inspection of a welded portion requires a cross-sectional image showing the cross-sectional shape of the welded portion.

While the non-destructive inspection method according to Japanese Unexamined Patent Publication No. JP2007-101329 described above makes it possible to know the interface shape of the welded portion on the basis of the interface depth of the welded portion measured at each of a plurality of measurement positions, there is a limit to stably obtaining the interface shape. This is because second-order harmonic waves contain reflected waves other than interface-reflected waves reflected by the welded interface depending on the measurement position since the incident angle of ultrasonic waves varies for each measurement position in order to measure the interface depth of the welded portion and, thus, it is difficult to extract only interface-reflected waves accurately and stably. In the case where second-order harmonic waves contain various reflected waves, a measurer chooses interface-reflected waves to measure the interface depth, and thus measurement values of the interface depth may vary depending on the skills of the measurer. Further, setting of the incident angle of ultrasonic waves at each measurement position is affected by the skills of the measurer, which is a factor that makes it difficult to stably measure the interface depth as mentioned above.

The present invention proposes an ultrasonic exploration method and an ultrasonic exploration apparatus that allow exploration of an exploration-target area such as a welded portion to provide a cross-sectional image of the exploration-target area accurately and stably.

Means for Solving the Problem

The present invention provides an ultrasonic exploration method configured to execute: an exploration process for executing an exploration operation, in which a transmission/reception position, at which ultrasonic waves at a specified frequency are transmitted to an exploration-target area of an exploration-target metal body and reflected waves of the ultrasonic waves are received, is sequentially changed by a specified pitch distance, for each of a plurality of preset incident angles of the ultrasonic waves, extracting harmonic waves contained in the reflected waves for each of the incident angles, and generating for each of the incident angles a nonlinear image of the exploration-target area in which echo signals acquired from the harmonic waves are presented on the basis of a response time from transmission of the ultrasonic waves to reception of the reflected waves; an image conversion process for converting the nonlinear image for each of the incident angles so as to conform to a frame form matching a cross-sectional shape of the exploration-target area on the basis of a refraction angle, at which the ultrasonic waves transmitted at the incident angle propagate in the exploration-target metal body, and the number of data prescribed in accordance with the refraction angle and a sonic speed of the ultrasonic waves to generate a frame conversion image for each of the incident angles; and an exploration image generation process for determining in advance a signal intensity threshold for removing echo signals resulting from an orientation defect due to a mismatched crystal orientation in a crystal structure of the exploration-target metal body, and overlapping frame conversion images formed by only echo signals whose signal intensity is the signal intensity threshold or more to generate a nonlinear exploration image of the exploration-target area.

In the case where a nonlinear image is generated in accordance with echo signals acquired from harmonic waves contained in reflected waves and the nonlinear image is corrected to match the cross-sectional shape of an exploration-target area on the basis of the exploration method according to Japanese Unexamined Patent Publication No. JP2007-101329 previously invented by the present inventors, a desired image showing the cross-sectional shape of the exploration-target area cannot be obtained. For example, in the case where a welded portion at which metal plates are welded to each other described above is explored as the exploration-target area, the nonlinear image shows a large amount of echo signals other than echo signals generated at the interface of the welded portion, and thus it is difficult to clearly show the interface shape of the welded portion. Further, in the case where the incident angle of ultrasonic waves is varied to generate the nonlinear image for each incident angle, each image presents different echo signals, and thus it is still more difficult to clearly show echo signals generated at the interface of the welded portion. For the purpose of addressing such issues to obtain an image in which the cross-sectional shape of a welded portion is clearly shown, the present inventors made diligent studies to find that harmonic waves contain defective reflected waves reflected by an orientation defect due to a mismatched crystal orientation in the crystal structure of metals, and therefore it is difficult to specify interface-reflected waves reflected by the interface of a welded portion. More specifically, metals have an imperfect crystal structure, and therefore have an orientation defect due to a mismatched crystal orientation caused by segregation in the parent metal or the like. Harmonic waves contain defective reflected waves reflected by such an orientation defect. The orientation defect is caused by a difference in crystal orientation, which can be diverse. Therefore, defective reflected waves may be generated, or may not be generated, depending on the hitting angle (refraction angle) of ultrasonic waves for each crystal orientation. Since harmonic waves may contain defective reflected waves reflected by an orientation defect and interface-reflected waves reflected by the interface of a welded portion mixed with each other as described above, it is difficult to clearly discriminate interface-reflected waves generated by the interface of the welded portion. An orientation defect may be caused by heat applied during welding, which, in the case where a welded portion is explored, can be a factor that makes it difficult to clearly discriminate the interface shape of the welded portion.

The present invention provides an ultrasonic exploration method invented on the basis of the findings described above, which includes generating a nonlinear image in which echo signals from harmonic waves are presented for each of a plurality of incident angles, converting each nonlinear image into a frame conversion image matching the cross-sectional shape of an exploration-target area in accordance with the refraction angle and the number of data, determining a signal intensity threshold for removing echo signals generated by an orientation defect described above, and overlapping frame conversion images formed by only echo signals whose signal intensity is the signal intensity threshold or more to generate a nonlinear exploration image as a cross-sectional image of the desired exploration-target area. In addition to finding that harmonic waves are generated by an orientation defect described above, the present inventors also found that the signal intensity of echo signals obtained from harmonic waves reflected by an orientation defect is low compared to a plane defect such as a crystal grain boundary, for example. The reason is considered that since an orientation defect is caused by a mismatched crystal orientation as described above, reflected waves reflected by an orientation defect are scattered and a part of the reflected waves is received as defective reflected waves. Then, the intensity of echo signals generated by an orientation defect is examined to determine the upper limit of the intensity as a signal intensity threshold, and only echo signals whose signal intensity is the signal intensity threshold or more are determined to be effective to remove echo signals whose signal intensity is less than the signal intensity threshold. This allows removal of echo signals generated by an orientation defect. Therefore, in the case where a welded portion is explored as the exploration-target area, for example, it is possible to provide a cross-sectional image of the welded portion in which echo signals generated by the interface of the welded portion are presented accurately and stably.

In the present invention, in the exploration process, an exploration operation in which the transmission/reception position is changed while holding a specified incident angle is repeatedly performed for each of a plurality of preset incident angles to generate a nonlinear image for each incident angle. Then, each nonlinear image is subjected to an image conversion process. Thereafter, echo signals whose signal intensity is less than the signal intensity threshold are removed to overlap the resulting images. According to the method, in the case where there is a portion at which only relatively weak reflected waves can be received with reflected waves reflected by the interface scattered, such as a welded portion having a curved interface, for example, it is possible to provide a nonlinear exploration image accurately showing a cross-sectional image of the interface shape by overlapping frame conversion images generated for each of a plurality of incident angles.

In an exploration operation performed for each incident angle, ultrasonic waves propagate along a refraction angle determined by the incident angle. Thus, in a nonlinear image for each incident angle, position information on reflected waves (echo signals) obtained in accordance with the response time of the reflected waves is presented as the depth along the propagation direction of ultrasonic waves (the distance from the transmission position of ultrasonic waves). In addition, the number of data along the propagation direction of ultrasonic waves is determined in accordance with the refraction angle and the sonic speed of ultrasonic waves in an exploration-target metal body. Therefore, in order to overlap nonlinear images for each incident angle as mentioned above, an image conversion process is performed to convert each nonlinear image so as to conform to a frame form matching the cross-sectional shape of the exploration-target area on the basis of the refraction angle and the number of data to generate a frame conversion image for each incident angle. The frame form matching the cross-sectional shape of the exploration-target area may include not only forms matching the exploration-target area in both cross-sectional shape and dimensional size but also similar forms obtained by expanding or contracting the cross-sectional shape at a specified dimensional ratio.

In the exploration image generation process described above, before determining echo signals whose signal intensity is the signal intensity threshold or more to be effective, the frame conversion images for each incident angle may be subjected to any of a Fourier transform, a fast Fourier transform, and a maximum entropy method. Such processes make it easy to discriminate echo signals due to an orientation defect still more clearly, and therefore make it easy to determine a signal intensity threshold for removing echo signals due to the orientation defect. Echo signals at the same position in the frame conversion images for each incident angle may be added or multiplied so that echo signals whose added or multiplied value is the signal intensity threshold or more are determined to be effective. Echo signals due to an orientation defect may be caused, or may not be caused, depending on the incident angle of ultrasonic waves as described above. Therefore, the addition or the multiplication makes it further easy to discriminate such echo signals. Furthermore, any of a Fourier transform, a fast Fourier transform, and a maximum entropy method may be appropriately combined with the addition or the multiplication of echo signals at the same position to further improve the accuracy of discrimination of echo signals due to an orientation defect. The signal intensity threshold may be appropriately changed in accordance with the process to be used.

The term "harmonic waves" as used herein refers collectively to multi-order harmonic waves such as second-order harmonic waves, third-order harmonic waves, and fourth-order harmonic waves. One or a plurality of such harmonic waves may be appropriately selected to be used.

In the ultrasonic exploration method described above, it is proposed that the image conversion process includes correcting, for each of the nonlinear images at each of the incident angles, an aspect ratio of a frame in which the nonlinear image is presented on the basis of the number of data prescribed in accordance with the pitch distance of the transmission/reception position for the ultrasonic waves and the number of data prescribed in accordance with the refraction angle and the sonic speed of the ultrasonic waves, and thereafter correcting an angle of each of the nonlinear images at each of the incident angles, in addition to the cross-sectional shape of the exploration-target area, in accordance with the refraction angle to generate a frame conversion image for each of the incident angles.

The nonlinear image generated by the exploration process is presented in a rectangular frame, with the short sides and the long sides of the frame respectively corresponding to a direction in which the transmission/reception position of ultrasonic waves is changed (hereinafter a "scanning direction") and a direction in which ultrasonic waves propagate in an exploration-target metal body (hereinafter an "ultrasonic wave propagation direction"). In the nonlinear image, the number of data along the scanning direction is prescribed in accordance with the pitch distance, and the number of data along the ultrasonic wave propagation direction is prescribed in accordance with the refraction angle and the sonic speed of ultrasonic waves. Also, the numbers of data in both directions are different from each other. The aspect ratio of the frame of the nonlinear image is corrected in accordance with the ratio between the number of data in the scanning direction and the number of data in the ultrasonic wave propagation direction. This allows the ratio between the length in the scanning direction and the length in the refraction direction of the nonlinear image to be matched with the ratio between the length in the scanning direction and the length in the refraction direction of the cross-sectional shape of the exploration-target area. There is a limit to the pitch distance of the transmission/reception position in consideration of accuracy, efficiency, and so forth. Thus, the number of data in the ultrasonic wave propagation direction is normally larger than the number of data in the scanning direction. Therefore, it is suitable to correct the length in the scanning direction of the frame of the nonlinear image using the length in the ultrasonic wave propagation direction as a reference. Consequently, the length in the ultrasonic wave propagation direction with a larger number of data is maintained, and therefore it is possible to maintain the image processing accuracy without reducing the number of data in the ultrasonic wave propagation direction.

Next, each nonlinear image which has been subjected to the aspect ratio correction described above is subjected to an angle correction so as to match the refraction angle. Each nonlinear image is presented in a rectangular frame as described above, with one side (the long side) of the frame being formed along the ultrasonic wave propagation direction. Thus, an angle correction is performed so as to match the one side with the refraction angle in order to obtain a parallelogram frame. Consequently, the nonlinear image can be matched with the cross-sectional shape of the exploration-target area in terms of orientation.

As a result of the image conversion process, a frame conversion image in a frame form matching the cross-sectional shape of the exploration-target area in frame aspect ratio and orientation is generated from each nonlinear image generated in the exploration process. Since the image conversion process is a quantitative conversion process based on the sonic speed and the refraction angle of ultrasonic waves described above, position information on echo signals presented in each nonlinear image is determined by quantitative values (coordinate position data) also in each frame conversion image. Further, correlation of position information on echo signals can be achieved between frame conversion images.

In the ultrasonic exploration method described above, it is proposed that the exploration image generation process includes, before overlapping the frame conversion images, correcting a size of frame conversion images other than a frame conversion image with the largest number of data so as to match the frame conversion images in frame size with the frame conversion image with the largest number of data.

Frame conversion images generated by the image conversion process have different frame sizes for each incident angle (refraction angle) as a result of the aspect ratio correction according to the number of data in the ultrasonic wave propagation direction described above. Thus, the size of the frame conversion images is corrected so as to match the same frame size before being overlapped. The size of frame conversion images other than a frame conversion image with the largest number of data is corrected so as to match the frame size of the frame conversion image with the largest number of data. Thus, the image processing accuracy can be maintained without reducing the number of data of the frame conversion image with the largest number of data. Then, the frame conversion images with the corrected size can be overlapped to obtain a high-precision nonlinear exploration image.

In the exploration image generation process, frame conversion images formed by echo signals whose signal intensity is the signal intensity threshold or more may be generated after performing such a frame size correction, or a frame size correction may be performed after frame conversion images formed by echo signals whose signal intensity is the signal intensity threshold or more are generated.

An ultrasonic exploration apparatus to which the ultrasonic exploration method according to the present invention described above is applicable includes: ultrasonic wave generation means for generating ultrasonic waves at a specified frequency; a probe including a transmission section that transmits the ultrasonic waves generated by the ultrasonic wave generation means and a reception section that receives reflected waves of the ultrasonic waves; probe scanning means for moving the probe so as to vary a transmission/reception position at which the ultrasonic waves are transmitted and the reflected waves are received; probe tilting means for tilting the probe so as to adjust an incident angle at which the ultrasonic waves are incident on an exploration-target metal body; scanning control means for performing an exploration operation, in which the transmission/reception position is sequentially changed by a specified pitch distance while holding the probe at a specified incident angle, for each of a plurality of preset incident angles by controlling operation of the probe scanning means and the probe tilting means; and exploration image processing means including: an image generation process content for extracting harmonic waves contained in the reflected waves from the reflected waves received by the probe for each of the incident angles to generate for each of the incident angles a nonlinear image in which echo signals acquired from the harmonic waves are presented on the basis of a response time from transmission of the ultrasonic waves to reception of the reflected waves; an image conversion process content for converting the nonlinear image for each of the incident angles so as to conform to a frame form matching a cross-sectional shape of the exploration-target metal body on the basis of a refraction angle, at which the ultrasonic waves transmitted at the incident angle propagate in the exploration-target metal body, and the number of data prescribed in accordance with the refraction angle and a sonic speed of the ultrasonic waves to generate a frame conversion image for each of the incident angles; and an exploration image generation process content for determining in advance a signal intensity threshold for removing echo signals resulting from an orientation defect due to a mismatched crystal orientation in a crystal structure of the exploration-target metal body, and overlapping frame conversion images formed by only echo signals whose signal intensity is the signal intensity threshold or more to generate a nonlinear exploration image of the exploration-target area.

Such a configuration has been achieved by finding that, since harmonic waves contain defective reflected waves generated by an orientation defect as described above, it is difficult to clearly show the interface shape of a welded portion, for example, in a nonlinear image in which echo signals acquired from the harmonic waves are presented. In such an apparatus, an exploration operation of a probe is performed in which the transmission/reception position at which ultrasonic waves are transmitted and reflected waves are received is changed by a specified pitch distance, and the exploration image processing means includes an image generation process content for generating a nonlinear image for each incident angle, an image conversion process content for converting each nonlinear image into a frame conversion image, and an exploration image generation process content for overlapping frame conversion images formed by only echo signals whose signal intensity is a signal intensity threshold or more to provide a desired nonlinear exploration image as a cross-sectional image of an exploration-target area. The thus obtained nonlinear exploration image can provide a clear presentation of the interface shape of a welded portion, for example, as the method described above. Thus, the welding shape can be determined easily and accurately in non-destructive inspection of the welded portion. Accordingly, the configuration can achieve the same functions and effects as those of the ultrasonic exploration method according to the present invention described above.

In the configuration, a nonlinear image is obtained by the image generation process content described above in accordance with the exploration operation performed by the scanning control means. The scanning control means controls operation of the probe in accordance with the pitch distance and a plurality of incident angles set in advance. Thus, a nonlinear image can be automatically obtained for each incident angle.

The transmission section and the reception section of the probe according to the configuration may be separate members disposed separately, or may be provided integrally with each other. The configuration may be further provided with a monitor that displays nonlinear images generated along with an exploration operation, frame conversion images generated by the image conversion process content, nonlinear exploration images generated by the exploration image generation process content, and so forth. Further, the monitor may display the process steps of the image conversion process content and the process steps of the exploration image generation process content to allow a measurer to perform operation.

EFFECT OF THE INVENTION

As described above, the present invention provides an ultrasonic exploration method in which an exploration operation, in which the transmission/reception position, at which ultrasonic waves are transmitted and received, is changed by a specified pitch distance, is performed for each of a plurality of incident angles, a nonlinear image in which echo signals acquired from harmonic waves of reflected waves are presented on the basis of the response time of the ultrasonic waves is generated for each incident angle, each nonlinear image is converted into a frame conversion image in accordance with the cross-sectional shape of an exploration-target area, and frame conversion images formed by only echo signals whose signal intensity is a signal intensity threshold, which is determined for removing echo signals generated by an orientation defect, or more are overlapped to generate a nonlinear exploration image of the exploration-target area. The method is achieved by finding that harmonic waves of reflected waves contain defective reflected waves generated by an orientation defect. According to such a method, echo signals resulting from defective reflected waves mentioned above can be removed using the signal intensity threshold. Therefore, it is possible to stably provide a nonlinear exploration image in which the cross-sectional shape of the exploration-target area is clearly shown by overlapping frame conversion images after the removal. Thus, according to the ultrasonic exploration method of the present invention, it is possible to provide a cross-sectional image of a welded portion of an automobile wheel described above, for example, as a nonlinear exploration image in which the interface shape of the welded portion is accurately presented, allowing easy and accurate inspection of the welded portion.

In the ultrasonic exploration method described above, in the case where the aspect ratio of the frame of the nonlinear image for each incident angle is corrected in accordance with the number of data prescribed in accordance with the pitch distance and the number of data prescribed in accordance with the refraction angle and the sonic speed of ultrasonic waves and thereafter an angle correction is performed in accordance with the refraction angle to generate a frame conversion image, it is possible to determine position information on echo signals in each frame conversion image by quantitative values (coordinate position data), and to achieve correlation of position information on echo signals between frame conversion images.

In the ultrasonic exploration method described above, in the case where the size of frame conversion images other than a frame conversion image with the largest number of data is corrected so as to match the frame size of the frame conversion image with the largest number of data before overlapping the frame conversion images, the largest number of data is maintained. Therefore, it is possible to maintain the image processing accuracy while preventing a reduction in number of data. Therefore, a high-precision nonlinear exploration image can be generated by overlapping the frame conversion images after correcting the size of the frame conversion images.

An ultrasonic exploration apparatus according to the present invention includes ultrasonic wave generation means, a probe including a transmission section and a reception section, probe scanning means for moving the probe, probe tilting means for tilting the probe, scanning control means for controlling operation of the probe scanning means and the probe tilting means so as to perform an exploration operation, in which the probe is moved by a specified pitch distance, for each of a plurality of incident angles. The exploration image processing means according to the present invention generates for each incident angle a nonlinear image in which echo signals acquired from harmonic waves of reflected waves are presented on the basis of the response time of the ultrasonic waves, converting each nonlinear image into a frame conversion image in accordance with the cross-sectional shape of an exploration-target area, and overlapping frame conversion images formed by only echo signals whose signal intensity is a signal intensity threshold, which is determined for removing echo signals generated by an orientation defect, or more to generate a nonlinear exploration image of the exploration-target area. The apparatus is achieved on the basis of the finding that harmonic waves of reflected waves contain defective reflected waves generated by an orientation defect. According to such a configuration, it is possible to stably provide a nonlinear exploration image in which the cross-sectional shape of the exploration-target area is clearly presented in the same way as the method described above. Then, by using the apparatus to the inspection of a welded portion of an automobile wheel described above, for example, it is possible to accurately and stably determine from the nonlinear exploration image whether or not the welded portion is adequate.

BRIEF DESCRIPTION OF THE DRAWINGS

FIG. 3 shows images generated in the case where an incident angle θa is +20 degrees, in which FIG. 3A shows a nonlinear image 31 generated by an exploration process, FIG. 3B shows a corrected image 31' with its frame aspect ratio corrected by an image conversion process, and FIG. 3C shows a frame conversion image 32a with its angle corrected by the image conversion process;

FIG. 4 shows images generated by the image conversion process, in which FIG. 4A shows a frame conversion image 32a at an incident angle θa of +20 degrees, FIG. 4B shows a frame conversion image 32b at an incident angle θa of 18 degrees, FIG. 4C shows a frame conversion image 32c at an incident angle θa of 16 degrees, and FIG. 4D shows a frame conversion image 32d at an incident angle θa of 4 degrees;

FIG. 5 shows images generated by the image conversion process, in which FIG. 5E shows a frame conversion image 32e at an incident angle θa of 0 degrees, FIG. 5F shows a frame conversion image 32f at an incident angle θa of −16 degrees, FIG. 5G shows a frame conversion image 32g at an incident angle θa of −18 degrees, and FIG. 5H shows a frame conversion image 32h at an incident angle θa of −20 degrees;

FIG. 6A shows a nonlinear exploration image 35 obtained by overlapping frame conversion images based on only echo signals whose signal intensity is a signal intensity threshold or more, and FIG. 6B shows a cross-sectional photograph of the exploration-target metal body 20;

FIG. 9A shows a comparative image 37 obtained by overlapping frame conversion images 32a to 32h of FIGS. 4 and 5, and FIG. 9B shows an image obtained by overlapping the comparative image 37 and a cross-sectional photograph of the exploration-target metal body 20.

DESCRIPTION OF THE PREFERRED EMBODIMENT

An embodiment of the present invention will be described in detail with reference to the accompanying drawings.

Figure 1:
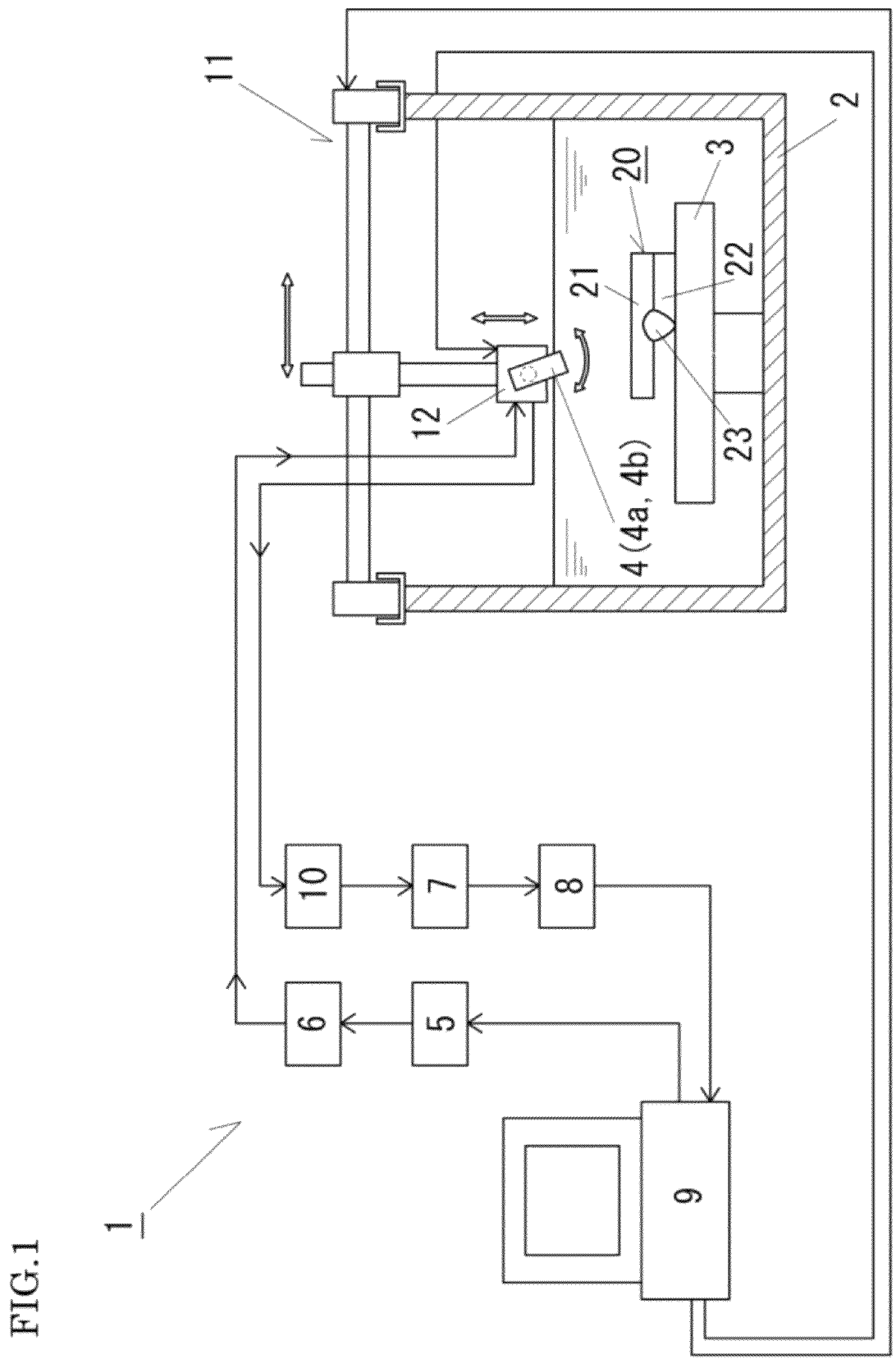
FIG. 1 is a schematic diagram of an ultrasonic exploration apparatus 1 according to an embodiment of the present invention.

FIG. 1 is a schematic diagram of an ultrasonic exploration apparatus 1 according to an embodiment of the present invention. The ultrasonic exploration apparatus 1 includes a water tank 2 provided with a placement table 3 for placement of an exploration-target metal body 20. The exploration-target metal body 20 is placed in water in the water tank 2. The ultrasonic exploration apparatus 1 also includes a probe 4 located in the water in the water tank 2 to transmit specified ultrasonic waves to the exploration-target metal body 20 and receive reflected waves of the ultrasonic waves.

The ultrasonic exploration apparatus 1 is provided with a probe scanning device 11 that moves the probe 4 described above upward and downward in the vertical direction and forward and rearward and leftward and rightward in the horizontal direction (a mechanism for forward and rearward movement in the horizontal direction is not shown). The probe 4 is movable vertically, horizontally, and obliquely in variable directions under control of vertical and horizontal movement performed by the probe scanning device 11. The ultrasonic exploration apparatus 1 is also provided with a probe tilting device 12 that tilts the probe 4 in one direction (in the left-right direction of the drawing sheet) with respect to the vertical axis of the probe 4. The probe 4 is attached to the probe scanning device 11 via the probe tilting device 12, and is movable in the variable directions and also tiltable.

The probe 4 described above includes a transmission section 4a that transmits ultrasonic waves and a reception section 4b that receives reflected waves of the ultrasonic waves, integrated with each other. That is, ultrasonic waves are transmitted and reflected waves are received generally at the same position. Therefore, in the embodiment, the position of the probe 4 in the horizontal direction and the vertical direction is defined as a transmission/reception position p at which ultrasonic waves are transmitted and reflected waves are received. Further, the probe 4 can be tilted by the probe tilting device 12 described above to appropriately change the direction in which ultrasonic waves are transmitted from the transmission section 4a of the probe 4. The reception section 4b of the probe 4 is configured to receive reflected waves that are in the opposite direction to the ultrasonic waves transmitted from the transmission section 4a. Therefore, the reception section 4b can always easily receive reflected waves that propagate in the opposite direction to the propagation direction of the ultrasonic waves transmitted from the transmission section 4a. The direction in which ultrasonic waves are transmitted vertically downward from the transmission section 4a of the probe 4 is defined as a reference transmission direction (X direction illustrated in FIG. 2), of the prove 4 and the angle formed by the direction in which ultrasonic waves are actually transmitted from the transmission section 4a and the reference transmission direction is defined as an incident angle θa (see FIG. 2) of the ultrasonic waves.

The ultrasonic exploration apparatus 1 further includes a high-frequency generator 5, an amplifier 6, an amplifier 10, a high-pass filter 7, an A/D converter 8, and a control processing device 9. The probe 4 is connected to the amplifier 6, which amplifies ultrasonic waves generated by the high-frequency generator 5 controlled by the control processing device 9 to a specified frequency, to transmit from the transmission section 4a the ultrasonic waves at the specified frequency input from the amplifier 6. In the embodiment, the high-frequency generator 5 and the amplifier 6 can generate ultrasonic waves at a frequency of 20 MHz or higher. In the present invention, further, it is required that harmonic waves at 40 MHz and 60 MHz, which are respectively twice and three times the frequency of the incident ultrasonic waves, can be received in order to exploit harmonic waves, such as second-order harmonic waves and third-order harmonic waves, of the reflected waves. Thus, the transmission section 4a of the probe 4 can transmit ultrasonic waves at 20 MHz or higher, and the reception section 4b of the probe 4 can reliably receive harmonic waves of 40 MHz or higher.

The probe 4 is further connected to the A/D converter 8 via the amplifier 10 and the high-pass filter 7 so that reflected waves received by the reception section 4b are input to the A/D converter 8 via the amplifier 10 and the high-pass filter 7. The A/D converter 8 converts the reflected waves input from the high-pass filter 7 into digital data. Reflected wave data digitalized by the A/D converter 8 are input to the control processing device 9.

The control processing device 9 described above comprehensively controls the ultrasonic exploration apparatus 1, and includes various input keys (not shown) that allow a measurer to input specified exploration conditions and a monitor (not shown) that outputs the exploration conditions and exploration results. The control processing device 9 further includes a central processing unit CPU, a storage device RAM, and a storage device ROM (not shown). The storage device ROM stores various operation programs for driving each of the high-frequency generator 5, the amplifier 6, the probe scanning device 11, and the probe tilting device 12 described above, various computation programs for computing the reflected wave data input via the A/D converter 8 to perform image processing, and so forth. The central processing unit CPU executes the operation programs and the computation programs at an appropriate timing.

The control processing device 9 drives the probe scanning device 11 to change the position of the probe 4 in the horizontal direction and the vertical direction, and to detect the position of the probe 4 as a separate position from a preset reference position (for example, scanning initial position O to be described later) using three-dimensional coordinate data in the horizontal direction and the vertical direction. The control processing device 9 further drives the probe tilting device 12 to tilt the probe 4 and to detect the incident angle θa of the ultrasonic waves as angle data. In the embodiment, a sensor (not shown) that detects the position of the probe 4 in the horizontal direction and the vertical direction and a sensor (not shown) that detects the tilt angle (incident angle θa) of the probe 4 are provided so that the control processing device 9 controls operation of the probe scanning device 11 and the probe tilting device 12 precisely and stably on the basis of an input signal from each of these sensors.

The reflected waves received by the reception section 4b of the probe 4 described above are formed of a large number of successive waves at specified intervals, and thus are input in accordance with the passage of time indicating the intervals of the waves. That is, the control processing device 9 described above processes the reflected waves as a waveform defined by an amplitude and a time axis indicating the passage of time. Therefore, the control processing device 9 includes a time counter (not shown) that counts up each specified unit time to enable measurement of the passage of time using the number of counts indicated by the time counter. The control processing device 9 successively measures a time (hereinafter a "response time") that passes from the transmission of ultrasonic waves from the transmission section 4a of the probe 4 to the reception of reflected waves by the reception section 4b in accordance with the number of counts indicated by the time counter.

As described above, the control processing device 9 is connected to each of the high-frequency generator 5, the amplifier 6, the probe scanning device 11, the probe tilting device 12, the amplifier 10, the high-pass filter 7, the A/D converter 8, and the probe 4 described above. The probe scanning device 11 serves as probe scanning means according to the present invention, and the probe tilting device 12 serves as probe tilting means according to the present invention. The high-frequency generator 5 and the amplifier 6 serve as ultrasonic wave generation means according to the present invention, and the control processing device 9 forms scanning control means and exploration image processing means according to the present invention.

Control of exploration of the exploration-target metal body 20 performed by the ultrasonic exploration apparatus 1 according to the embodiment will be described next.

Figure 2:
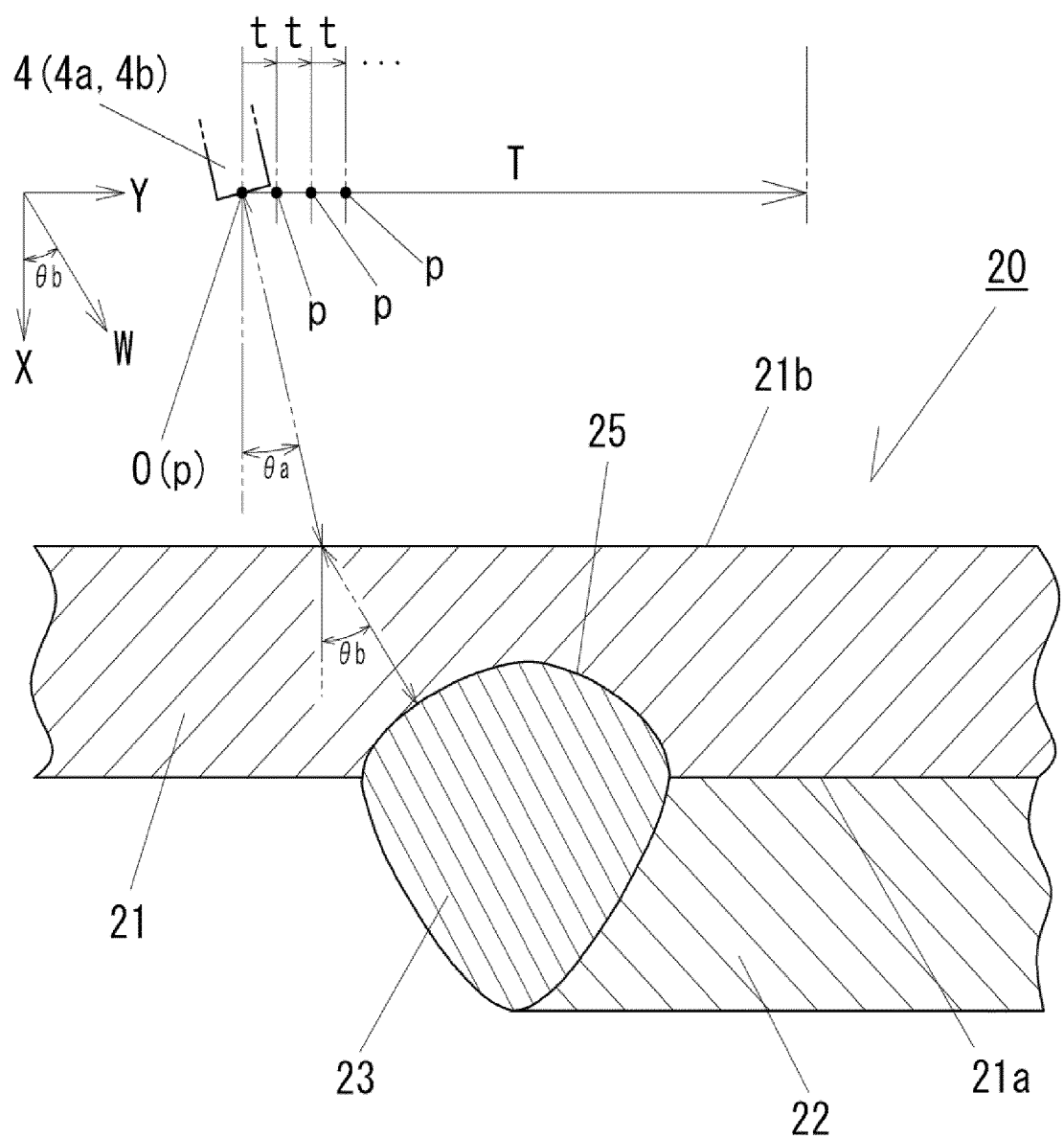
FIG. 2 illustrates the relationship between a probe 4 that transmits ultrasonic waves and an exploration-target metal body 20.

In the embodiment, the exploration-target metal body 20 is obtained by performing lap joint welding on two steel plates 21 and 22. The exploration-target metal body 20 is discussed in detail. A plate end of one steel plate 22 and a front surface 21a of the other steel plate 21 are subjected to fillet welding to form a welded portion 23 along the plate end of the steel plate 22 (see FIG. 2). When the exploration-target metal body 20 is cut along the transverse direction (Y direction in FIG. 2) generally perpendicular to the welding direction (longitudinal direction) of the welded portion 23 to observe the cut surface of the welded portion 23, the welded portion 23 is formed to be welded relatively deep into the steel plate 21 as shown in FIG. 2. In the steel plate 21, the welded portion 23 is formed to swell toward a back surface 21b of the steel plate 21. An interface 25 which is the boundary between a portion of the steel plate 21 at which the welded portion 23 is not formed and the welded portion 23 is also curved toward the back surface of the steel plate 21. In the embodiment, the welded portion 23 of the exploration-target metal body 20 serves as an exploration-target area according to the present invention.

The exploration-target metal body 20 described above is placed on the placement table 3 in the water tank 2 filled with water with the steel plate 21 above the steel plate 22 and with the back surface 21b extending generally along the horizontal direction (see FIGS. 1 and 2). At this time, the exploration-target metal body 20 is submerged under the water in the water tank 2.

Thereafter, the control processing device 9 sets the incident angle θa of the ultrasonic waves, the scanning initial position O of the probe 4, a scanning range T of the probe 4, a pitch distance t of the transmission/reception position p, and so forth. The incident angle θa of the ultrasonic waves is set to an angular range in which the ultrasonic waves are adequately incident into the exploration-target metal body 20, and in which the reflected waves do not contain vertical waves and horizontal waves mixed with each other. Such an angular range is different among metal materials, and thus is set in accordance with the metal material forming the exploration target.

The scanning initial position O and the scanning range T of the probe 4 are set in accordance with the exploration-target metal body 20 placed in the water tank 2 described above. Therefore, the scanning initial position O and the scanning range T of the probe 4 are appropriately set in accordance with the size of the exploration-target metal body 20, the size of the welded portion 23 as the exploration target, and the arrangement of the exploration-target metal body 20 on the placement table 3. In the embodiment, as shown in FIG. 2, the scanning initial position O is set such that the probe 4 moves horizontally in the direction (lateral direction Y) perpendicular to the welding direction of the welded portion 23 of the exploration-target metal body 20, and the scanning range T is set such that the probe 4 advances from the scanning initial position O in the lateral direction Y by a specified distance. The number of transmission/reception positions p in the scanning range T mentioned above is determined by setting the pitch distance t of the transmission/reception position p. A short pitch distance t increases the number of transmission/reception positions p to improve the exploration accuracy, but also increases the time required for the exploration. Thus, it is suitable to set the pitch distance t in consideration of the exploration accuracy and the efficiency.

In the case of a product such as an automobile wheel, for example, the incident angle θa of ultrasonic waves, the scanning initial position O of the probe 4, the scanning range T of the probe 4, the pitch distance t of the transmission/reception position p, and so forth described above may be set and stored in advance in accordance with the size or the standards of the product so that appropriate set values are selected to be used.

Thereafter, the probe 4 is immersed into the water in the water tank 2 to be positioned at the scanning initial position O described above. Then, the control processing device 9 controls operation of the probe tilting device 12 to tilt and hold the probe 4 at an angle selected from a plurality of incident angles θa set in advance. Thereafter, the control processing device 9 controls operation of the probe scanning device 11 to horizontally move the probe 4 intermittently in accordance with the pitch distance t described above in the lateral direction Y perpendicular to the welding direction of the welded portion 23 of the exploration-target metal body 20. Along with controlling operation of the probe scanning device 11, the control processing device 9 further transmits ultrasonic waves at 20 MHz generated by the high-frequency generator 5 and amplified by the amplifier 6 from the transmission section 4a of the probe 4 with the probe 4 temporarily stopped at the transmission/reception position p on the basis of the pitch distance t described above. The control processing device 9 then receives reflected waves of the ultrasonic waves, which are received from the reception section 4b of the probe 4 and input via the amplifier 10, the high-pass filter 7, and the A/D converter 8. Accordingly, the control processing device 9 stops the probe 4 at each transmission/reception position p described above for a specified period so that ultrasonic waves are transmitted and reflected waves are received sufficiently.

Then, when the probe 4 is moved and temporarily stopped at intervals of the pitch distance t described above to move over the scanning range T described above, the probe 4 is raised away from the exploration-target metal body 20 and returned to the scanning initial position O. Further, the control processing device 9 also controls transmission of ultrasonic waves and reception and input of reflected waves at each transmission/reception position p along with a sequence of operation for changing the transmission/reception position p on the basis of the pitch distance t while holding the specified incident angle θa. The operation for changing the transmission/reception position p on the basis of the pitch distance t is repeatedly executed for each of the plurality of incident angles θa set in advance to store data on the reflected waves input at each transmission/reception position p for each incident angle θa.

When reflected waves are input via the reception section 4b of the probe 4, further, the control processing device 9 extracts harmonic waves (multi-order harmonic waves such as second-order harmonic waves, third-order harmonic waves, and fourth-order harmonic waves) from the reflected waves input at each transmission/reception position p for each incident angle θa, and acquires echo signals 41 from the harmonic waves to generate nonlinear images 31 (nonlinear images 31 other than the one with an incident angle θa of 20 degrees are not shown) in which the echo signals 41 are presented (see FIG. 3A). More specifically, in the reflected waves input at each transmission/reception position p, waves at frequencies an integer times the fundamental frequency overlap each other to be presented as nonlinear ultrasonic waves in which the waveform at the fundamental frequency is distorted. When the reflected waves digitalized by the A/D converter 8 are input, the control processing device 9 performs a Fourier analysis on the reflected waves to decompose the reflected waves into fundamental-frequency waves, second-order harmonic waves, third-order harmonic waves, fourth-order harmonic waves, and so forth. The control processing device 9 then extracts the harmonic waves at twice, three times, four times, and so forth the fundamental frequency. The control processing device 9 further acquires a waveform signal forming the harmonic waves as a plurality of echo signals 41 generated in accordance with the frequency. The control processing device 9 also measures the response time required from the transmission of ultrasonic waves to the reception of reflected waves to calculate the depth at which each of the echo signals 41 was generated as the distance from the probe 4 on the basis of the response time and the sonic speed of the ultrasonic waves. The control processing device 9 then generates a nonlinear image 31 (see FIG. 3A) in which the plurality of echo signals 41 acquired at each transmission/reception position p are presented in accordance with the generation depth. Each echo signal 41 represents a signal intensity (wave energy), and the nonlinear image 31 presents the signal intensity by a color representation with a plurality of gradations. The nonlinear image 31 is formed by a rectangular frame, with its lateral direction Y corresponding to the scanning direction of the transmission/reception position p (lateral direction Y perpendicular to the welding direction) described above and with its longitudinal direction W corresponding to the direction of depth at which the echo signals 41 are generated (an ultrasonic wave propagation direction W to be discussed later) (see FIG. 3A). That is, the nonlinear image 31 is formed by arranging a plurality of echo signals 41 in a row in the longitudinal direction W, and arranging rows of the echo signals 41, the number of which is the same as the number of the transmission/reception positions p, in the lateral direction Y.

The process for generating a nonlinear image 31 is performed for each incident angle θa to generate a nonlinear image 31 for each incident angle θa (nonlinear images 31 other than the one with an incident angle θa of 20 degrees are not shown). The ultrasonic waves are refracted when they enter into the exploration-target metal body 20, and a refraction angle θb is determined in accordance with the incident angle θa. Then, the ultrasonic wave propagate along the direction of the refraction angle θb, and reflected waves returning along the direction of the refraction angle θb are received. Thus, the generation depth of each echo signal 41 calculated on the basis of the response time and the sonic speed is calculated as the distance from the probe 4 along the direction W of the refraction angle θb (which is the same as the ultrasonic wave propagation direction). Therefore, the longitudinal direction W of the frame is different among the nonlinear images 31 generated for each incident angle θa. The computation process for calculating the depth of each echo signal 41 on the basis of the response time and the sonic speed may be the same as processing methods according to the related art (an example of which is disclosed in Japanese Unexamined Patent Publication No. JP2007-101329), and therefore is not described herein.

The process in which the probe 4 performs an exploration operation for each incident angle θa to generate a nonlinear image 31 for each incident angle θa is an exploration process according to the present invention. The control processing device 9 stores and holds computation programs, data, and so forth as an exploration process content for executing the exploration process, and appropriately reads the programs, data, and so forth to execute the exploration process.

Next, the control processing device 9 converts the nonlinear images 31 for each incident angle θa (nonlinear images 31 other than the one with an incident angle θa of 20 degrees are not shown) so as to conform to a frame form matching the cross-sectional shape of the welded portion 23 of the exploration-target metal body 20 (see FIGS. 3A and 3B). This process is an image conversion process according to the present invention. The control processing device 9 stores and holds computation programs, data, and so forth as an image conversion process content for executing the image conversion process, and reads the programs, data, and so forth to execute the image conversion process.

In the image conversion process, first, the aspect ratio of the rectangular frame forming the nonlinear image 31 for each incident angle θa is corrected on the basis of the number of pixels in the lateral direction (scanning direction) prescribed in accordance with the pitch distance t of the transmission/reception position p for ultrasonic waves and the number of pixels in the longitudinal direction (ultrasonic wave propagation direction) prescribed in accordance with the refraction angle and the sonic speed of ultrasonic waves in the exploration-target metal body 20 (see FIG. 3B). In the embodiment, the number of pixels is used as a number of data according to the present invention. More specifically, the number of pixels in the longitudinal direction and the number of pixels in the lateral direction in the unit square area of the nonlinear images 31 (see FIG. 3A) are calculated. The number of pixels in the lateral direction is determined by the pitch distance t described above. Therefore, in the embodiment, the number of pixels in the lateral direction is the same for all the nonlinear images 31 (nonlinear images 31 other than the one for an incident angle θa of 20 degrees are not shown). Meanwhile, the number of pixels in the longitudinal direction is calculated in accordance with the frequency of ultrasonic waves, the refraction angle θb of ultrasonic waves in the exploration-target metal body 20, and a sonic speed Vb of ultrasonic waves in the exploration-target metal body 20. The refraction angle θb is calculated in accordance with "Snell's law" indicated by Formula (1) below. The number of pixels in the longitudinal direction is calculated in accordance with Formula (2) below. The thus calculated number of pixels in the longitudinal direction is different among the incident angles θa, and thus calculated for each nonlinear image 31.

$$(\sin \theta a / Va) = (\sin \theta b / Vb) \tag{1}$$

$$(\text{Number of pixels}/S) = \text{frequency}/(Vb/2 \times \cos \theta b \times 1000) \text{ [pixels/mm]} \tag{2}$$

In Formula (1) above, Va represents the sonic speed of ultrasonic waves in the water. In Formula (2), S represents the length of a side of the unit square area. The sonic speed Vb of ultrasonic waves in the exploration-target metal body 20 is different among metal materials, and thus obtained in advance through actual measurement. Since the reflected waves are received as vertical waves or horizontal waves in accordance with the incident angle θa of the ultrasonic waves, the sonic speed of the vertical waves and the sonic speed of the horizontal waves are respectively obtained through actual measurement to appropriately use one of the sonic speed of the vertical waves and the sonic speed of the horizontal waves as the sonic speed Vb.

When the number of pixels in the longitudinal direction and the number of pixels in the lateral direction are calculated for each nonlinear image 31 at each incident angle θa, the aspect ratio of the rectangular frame of each nonlinear image 31 is corrected in accordance with the ratio between the number of pixels in the longitudinal direction and the number of pixels in the lateral direction. Consequently, the aspect ratio of the frame of a corrected image 31' (see FIG. 3B) obtained after the correction is matched with the aspect ratio of the cross-sectional shape of the welded portion 23 of the exploration-target metal body 20. In the process for correcting the aspect ratio mentioned above, the longitudinal length of the frame is maintained and the lateral length of the frame is corrected using the longitudinal length of the frame as a reference since the number of pixels in the longitudinal direction is larger than the number of pixels in the lateral direction. This is for the purpose of preventing a reduction in number of pixels in the longitudinal direction which is larger by matching the number of pixels in the longitudinal direction with the number of pixels in the longitudinal direction. Consequently, the number of pixels in the longitudinal direction of the nonlinear image 31 is maintained in the image after the correction of the aspect ratio, allowing high-precision image processing.

After the aspect ratio of each nonlinear image 31 is corrected as described above, the angle of each nonlinear image 31 is corrected in accordance with the refraction angle θb. The longitudinal direction W of the corrected image 31' (see FIG. 3B) obtained by correcting the aspect ratio of each nonlinear image 31 is the direction along the refraction angle θb (ultrasonic wave propagation direction) as described above. Therefore, the longitudinal direction W is tilted in accordance with the refraction angle θb. As a result of this process, the image with the corrected aspect ratio mentioned above is converted from the rectangular frame into a parallelogram frame such that the longitudinal direction (vertical direction) X of the frame matches the vertical direction X of the cross-sectional shape of the welded portion 23 of the exploration-target metal body 20.

Accordingly, each nonlinear image 31 (see FIG. 3A) is converted so as to conform to a frame form matching the cross-sectional shape of the welded portion 23 of the exploration-target metal body 20 by performing a process for correcting the aspect ratio and a process for changing the angle in accordance with the refraction angle θb on each nonlinear image 31. Consequently, a frame conversion image 32a (see FIG. 3C) is obtained for each incident angle θa.

Next, the control processing device 9 overlaps frame conversion images 32a to 32h for each incident angle θa to generate a nonlinear exploration image 35 (see FIG. 6A) as a cross-sectional image of the welded portion 23 of the exploration-target metal body 20. This process is an exploration image generation process according to the present invention. The control processing device 9 stores and holds computation programs, data, and so forth as an exploration image generation process content for executing the exploration image generation process, and reads the programs, data, and so forth to execute the exploration image generation process.

In the exploration image generation process, first, each of the frame conversion images 32a to 32h (see FIGS. 4 and 5) for each incident angle θa is subjected to a fast Fourier transform. Thereafter, echo signals 41 at the same coordinate position in any two of the frame conversion images (32a to 32h) are multiplied to extract only echo signals 41a for which the resulting product is a predetermined signal intensity threshold or more and to remove the other echo signals 41. In the nonlinear image 31 generated by the exploration operation described above, position information on each echo signal 41 is indicated by the depth (distance from the probe 4) in the longitudinal direction (ultrasonic wave propagation direction) and the position (transmission/reception position p) in the lateral direction (scanning direction). In the image conversion process in which each nonlinear image 31 (nonlinear images 31 other than the one with an incident angle θa of 20 degrees are not shown) are converted into the frame conversion images 32a to 32h, the process for correcting the aspect ratio of the frame and the process for correcting the angle are executed in accordance with quantitative values. Therefore, also in the frame conversion images 32a to 32h, position information on each echo signal 41 is represented as quantitative position information (hereinafter referred to as "coordinate position data") represented in a two-dimensional coordinate system defined by the horizontal direction and the vertical direction.

The signal intensity threshold described above is discussed in detail. In the nonlinear images 31 (see FIG. 3A) and the frame conversion images 32a to 32h (see FIGS. 4 and 5), not only echo signals 41 generated at the back surface 21b of the exploration-target metal body 20 and echo signals 41 generated at the interface 25 of the welded portion 23, but also other echo signals 41 are shown. Therefore, it is difficult to specify the interface 25 of the welded portion 23 from each of the frame conversion images 32a to 32h (see FIGS. 4 and 5). Thus, in the case where it is attempted to specify the interface 25, the skills of the measurer must be relied upon, which sets a limit to the accuracy and the stability of the resulting image showing the interface 25 of the welded portion 23. In view of such circumstances, the present inventors made diligent studies to find that an orientation defect having a mismatched crystal orientation existed in the crystal structure of a parent metal and harmonic waves contained defective reflected waves reflected by the orientation defect. As a result of further studies, it was found that an orientation defect was caused by a difference in crystal orientation and a part of reflected waves diffusely reflected by the orientation defect (defective reflected waves) were received, and thus defective reflected waves reflected by the orientation defect were generated or were not generated depending on the hitting angle of ultrasonic waves (refraction angle θb). An orientation defect is caused by a difference in crystal orientation due to segregation in a parent metal, influence of welding heat, or the like. Incidentally, in an ultrasonic exploration method based on a pulse-echo method according to the related art, a signal reflected by a defect such as a minute void, for example, is detected as reflected waves, and thus a signal reflected by an orientation defect mentioned above is not shown. That is, it was first found in the course of achieving the present invention that harmonic waves contained defective reflected waves reflected by an orientation defect mentioned above. With such findings, it became necessary to remove echo signals 41 representing defective reflected waves in order to obtain an interface image of the welded portion 23 using the frame conversion images 32a to 32h mentioned above (see FIGS. 4 and 5). Thus, a signal intensity threshold serving as a threshold for the signal intensity of the echo signals 41 was determined in order to remove echo signals 41 generated by an orientation defect. Echo signals 41 generated by an orientation defect are part of echo signals diffusely reflected by the orientation defect, and thus have a relatively small signal intensity. Based on this, the signal intensity threshold for removing echo signals 41 generated by an orientation defect is determined. The signal intensity threshold is suitably determined as an empirically obtained value, and may be determined theoretically on the basis of experience of comparing the frame conversion images 32a to 32h described above and actual cross-sectional photographs, for example.

Figure 4:
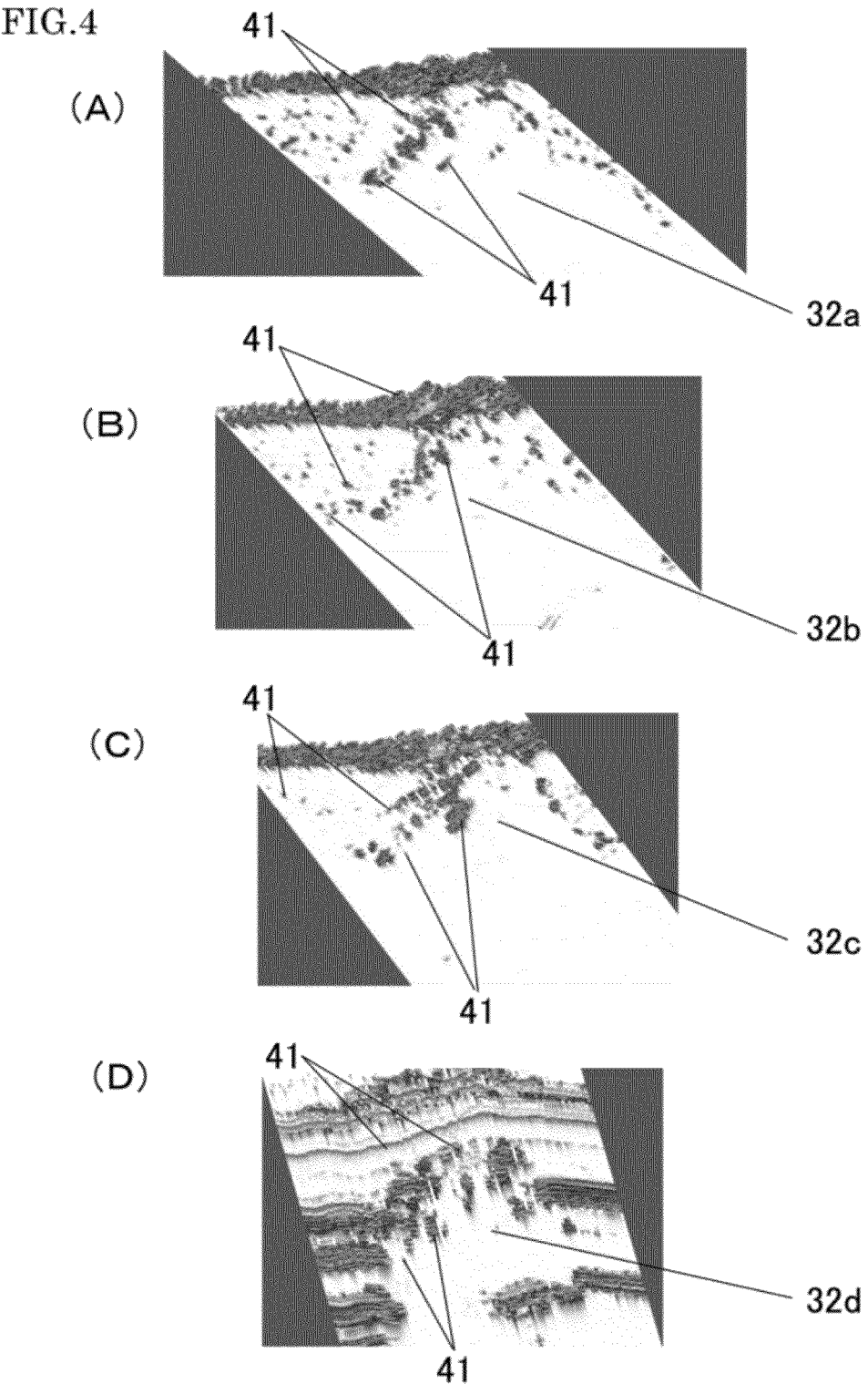

The thus determined signal intensity threshold is used to determine the product obtained by multiplying echo signals 41 at the same coordinate position in any of the two frame conversion images (32a to 32h) shown in FIGS. 4 and 5. Then, only echo signals 41a for which the resulting product is the signal intensity threshold or more are determined to be effective, and all the other echo signals 41 are removed from the frame conversion images (32a to 32h). In the case where there is no echo signal 41 at the same coordinate position in one of the two frame conversion images, the product is calculated to be "0". In the frame conversion images (not shown) after this process, echo signals 41 generated by an orientation defect described above have been removed. The process for multiplying echo signals 41 at the same coordinate position in any two of the frame conversion images (32a to 32h) to determine only echo signals 41a for which the resulting product is the signal intensity threshold or more to be effective as described above is executed for all combinations of the frame conversion images (32a to 32h).

Thereafter, all the frame conversion images (not shown) formed by only the echo signals 41a are adjusted to have the same frame size. These frame conversion images are different in number of pixels in the ultrasonic wave propagation direction, and hence in frame size, in accordance with the incident angle θa. Such differences occur because the images may be generated by echo signals 41 acquired from vertical waves or horizontal waves of the reflected waves in accordance with the incident angle θa, and because the difference in refraction angle θb results in a difference in propagation amount of ultrasonic waves in a certain period even at the same sonic speed Vb. The frame conversion images with different frame sizes are adjusted to have the frame size of a frame conversion image with the largest number of pixels. That is, frame conversion images other than a frame conversion image with the largest number of pixels are expanded to have the frame size of the frame conversion image with the largest number of pixels. This is for the purpose of maintaining the frame size of the frame conversion image with the largest number of pixels, which is the largest, to prevent a reduction in number of pixels of the frame conversion image with the largest number of pixels. This allows high-precision image processing since the largest number of pixels are maintained.

All the frame conversion images (not shown) with their size corrected as described above are overlapped to generate a nonlinear exploration image 35 (see FIG. 6A). In the nonlinear exploration image 35, echo signals 41 generated by an orientation defect described above have been removed, and the interface shape of the welded portion 23 is clearly shown. In the embodiment, elements other than an element with the largest number of pixels are adjusted to the element with the largest number of pixels in the aspect ratio correction process and the frame size correction process in the image conversion process described above. Thus, the image accuracy is high, and the interface shape of the welded portion 23 is shown with high accuracy. In the nonlinear exploration image 35, further, echo signals 41a are shown using coordinate position data based on the response time of ultrasonic waves as described above. Thus, the welding depth of the welded portion 23 can also be calculated quantitatively.

Then, the nonlinear exploration image 35 (see FIG. 6A) may be printed for use as an inspection document to allow the interface shape and the welding depth of the welded portion 23 to be confirmed at a glance. Therefore, quality control of the welded portion 23 can be performed with high accuracy and usability. Moreover, the ultrasonic exploration apparatus 1 performs non-destructive inspection. Thus, the manufacturing cost can be reduced with no need to destroy a product.

Figure 7:
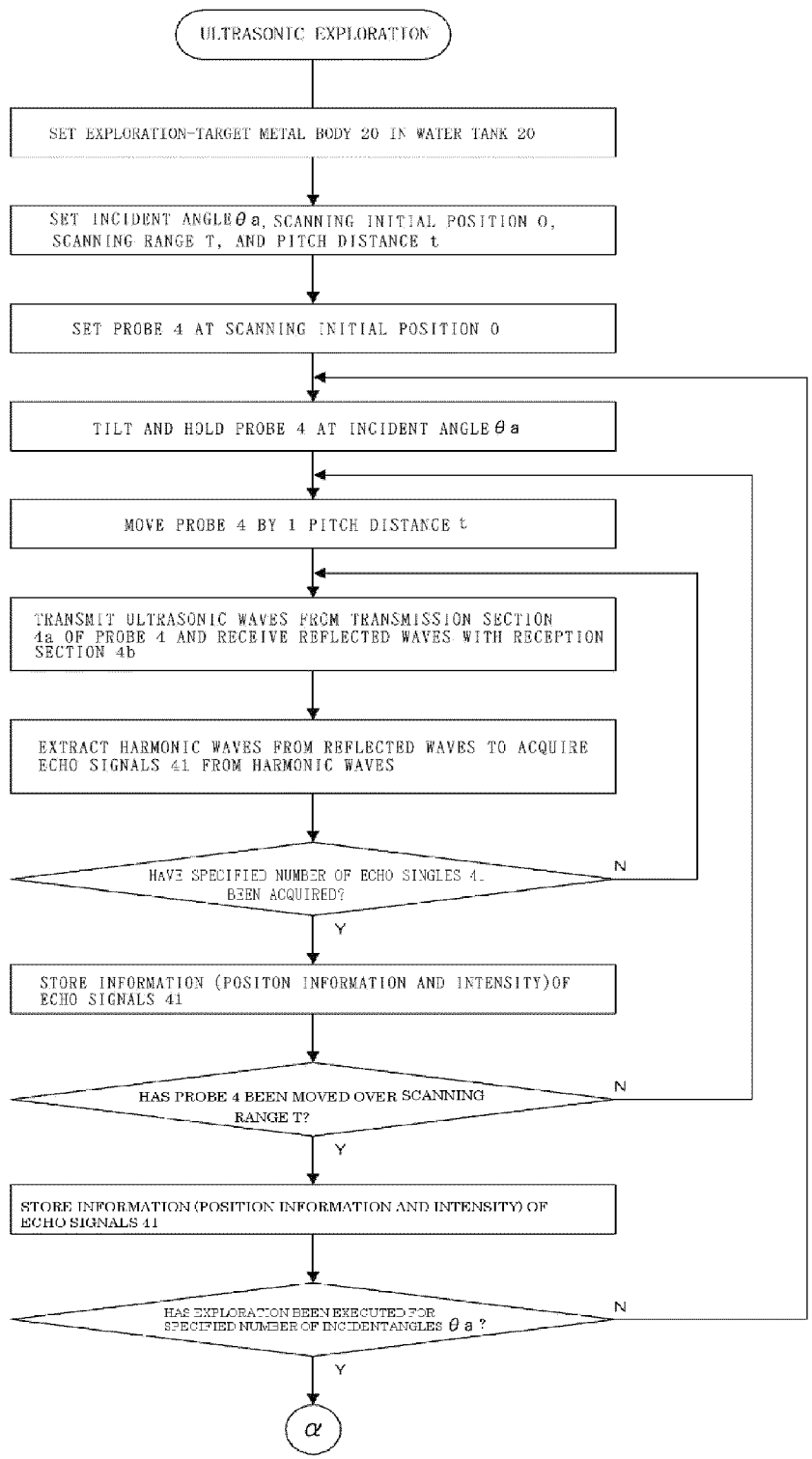
FIG. 7 is a flowchart showing steps for exploring the exploration-target metal body 20 using the ultrasonic exploration apparatus 1.
Figure 8:
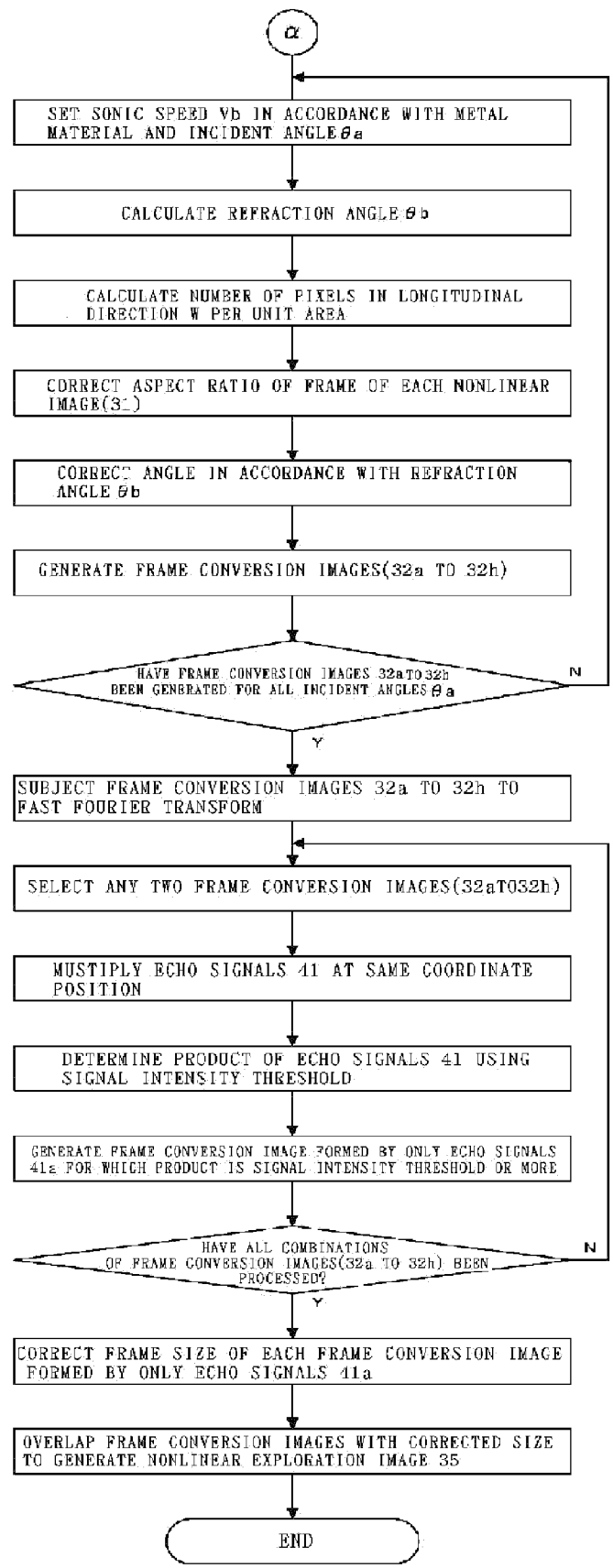
FIG. 8 is a flowchart showing steps for exploring the exploration-target metal body 20 which follow the steps of FIG. 7.

A description will be made of a process in which the exploration-target metal body 20 obtained by welding the two steel plates 21 and 22 to each other as described above is explored by the ultrasonic exploration apparatus 1 according to the embodiment. The exploration process proceeds in accordance with the flowcharts of FIGS. 7 and 8.

The exploration-target metal body 20 is obtained by subjecting the two steel plates 21 and 22 to fillet welding by arc welding (see FIGS. 2 and 6B) as described above. The steel plates 21 and 22 are each an SPFH590 (a hot-rolled steel plate for automobile structure). When the sonic speed of ultrasonic waves that propagate in the steel plates 21 and 22 is measured, the sonic speed of vertical waves is 6000 msec, and the sonic speed of horizontal waves is 3300 msec. In the exploration operation controlled by the control processing device 9 described above, the incident angle θa of the ultrasonic waves, the scanning initial position O of the probe 4, the scanning range T of the probe 4, the pitch distance t of the transmission/reception position p, and so forth are set. The scanning range T of the probe 4 is set to 10 mm along the direction perpendicular to the welded portion 23, and the scanning initial position O of the probe 4 is accordingly set as shown in FIG. 2. This allows the probe 4 to move transversely with respect to the welded portion 23. Also, the pitch distance t of the transmission/reception position p is set to 0.1 mm, and the transmission/reception position p is set to 100 locations in the scanning range T. The incident angle θa of ultrasonic waves is defined with respect to the advancing direction of the probe 4 in the vertical direction (reference transmission direction), and is set to a total of nine angles, namely 0 degrees (vertical direction), ±4 degrees, ±16 degrees, ±18 degrees, and ±20 degrees. In the case of the steel plates 21 and 22, inspection is performed using vertical waves in a range in which the incident angle θa is 0 degrees (vertical direction) to ±8 degrees, and using horizontal waves in a range in which the incident angle θa is ±14 degrees to ±27 degrees. In a range in which the incident angle θa is more than ±8 degrees and less than ±14 degrees, the reflected waves contain vertical waves and horizontal waves mixed with each other, and therefore it is difficult to perform accurate exploration. Meanwhile, in a range in which the incident angle θa exceeds ±27 degrees, the ultrasonic waves do not enter into the steel plate 21 but propagate on the back surface 21b, and therefore exploration cannot be performed.

The exploration-target metal body 20 is placed on the placement table 3 in the water tank 2 filled with water with the steel plate 21 above the steel plate 22 and with the back surface 21b extending generally along the horizontal direction as described above (see FIGS. 1 and 2). Then, the measurer starts the control processing device 9 to start an exploration operation for the welded portion 23 of the exploration-target metal body 20. The control processing device 9 executes the exploration process described above to perform an exploration operation in which the probe 4 is tilted and held at an incident angle θa of any of the above set angles (for example, +20 degrees) and intermittently changed in position in accordance with the pitch distance t from the scanning initial position O described above. Each time the probe 4 is moved by one pitch distance t to a transmission/reception position p, the probe 4 transmits ultrasonic waves at a frequency of 20 MHz and receives reflected waves. Then, the received reflected waves are subjected to data processing to store reflected wave data in the storage device RAM together with position information on the transmission/reception position p. Such transmission of ultrasonic waves and reception of reflected waves are performed each time the probe 4 is moved by one pitch distance t to obtain position information on 100 locations and reflected wave data for each transmission/reception position p. Then, as described above, the reflected wave data are subjected to a Fourier transform to extract harmonic waves, and a plurality of echo signals 41 are acquired from the harmonic waves. Each echo signal 41 represents a signal intensity, and the generation position of each echo signal 41 is determined as position information (coordinate position data) defined by the distance (depth) in the ultrasonic wave propagation direction and the transmission/reception position p calculated in accordance with the response time from the transmission to the reception of ultrasonic waves and the sonic speed. Then, all the echo signals 41 acquired in the scanning range T described above are arranged on a rectangular frame with its lateral direction corresponding to the scanning direction of the probe 4 and its longitudinal direction corresponding to the ultrasonic wave propagation direction mentioned above to generate a nonlinear image 31 (see FIG. 3A). In the nonlinear image 31, the signal intensity of each echo signal 41 is represented distinctively in a staged manner using the display color to allow confirmation of the intensity of the echo signals 41.

The exploration operation in which the probe 4 is held at a specified incident angle θa and intermittently changed in position by the pitch distance t as described above is performed for each of the set incident angles θa described above to obtain a nonlinear image 31 for each incident angle θa. That is, in the embodiment, nine nonlinear images 31 (nonlinear images 31 other than the one with an incident angle θa of 20 degrees are not shown) are generated. Then, data forming each nonlinear image 31 (such as the echo signals 41 and the coordinate position data on the echo signals 41) are stored in the storage device RAM.

When the nonlinear images 31 for each incident angle θa (nonlinear images 31 other than the one with an incident angle θa of 20 degrees are not shown) are obtained, the control processing device 9 performs the image computation process described above to convert each nonlinear image 31 so as to conform to a frame form matching the cross-sectional shape of the welded portion 23 of the exploration-target metal body 20. This is performed by calculating the refraction angle θb and the number of pixels in the longitudinal direction (ultrasonic wave propagation direction) for each nonlinear image 31 using Formulas (1) and (2) given above. In the case where the incident angle θa is any of 0 degrees and ±4 degrees, the refraction angle θb is calculated on the assumption that the sonic speed Vb in the steel plates 21 and 22 is 6000 msec. Meanwhile, in the case where the incident angle θa is any of ±16 degrees, ±18 degrees, and ±20 degrees, the refraction angle θb is calculated on the assumption that the sonic speed Vb is 3300 msec. The sonic speed of ultrasonic waves in the water is defined as 1500 msec. Then, as described above, the aspect ratio of the frame of each nonlinear image 31 is corrected in accordance with the ratio between the number of pixels in the longitudinal direction and the number of pixels in the lateral direction. Consequently, the aspect ratio of the frame of each nonlinear image 31 is matched with the aspect ratio of the cross-sectional shape of the welded portion 23 of the exploration-target metal body 20.

The angle of each corrected image 31' (see FIG. 3B) with the corrected aspect ratio is corrected in accordance with the refraction angle θb. In the frame of each nonlinear image 31, as described above, the longitudinal direction corresponds to the ultrasonic wave propagation direction, and the lateral direction corresponds to the scanning direction (horizontal direction). Therefore, as a result of this process, only the longitudinal direction is tilted by each refraction angle θb while maintaining the lateral direction at the horizontal direction. Consequently, each corrected image 31' (nonlinear images 31 other than the one with an incident angle θa of 20 degrees are not shown) is converted from a rectangular frame into a parallelogram frame (frame conversion images 32a to 32h) so that the vertical direction after the conversion matches the vertical direction of the exploration-target metal body 20.

A case where the incident angle θa is +20 degrees is described as an example. A nonlinear image 31 at an incident angle θa of +20 degrees is shown in FIG. 3A. When the incident angle θa is +20 degrees, the refraction angle θb is calculated to be 48.8 degrees using Formula (1). The number of pixels in the longitudinal direction W per 1 mm² is calculated to be 184 using Formula (2). Since the pitch distance t is 0.1 mm, the number of pixels in the lateral direction Y per 1 mm² is 10. The number of pixels in the longitudinal direction W is larger than the number of pixels in the lateral direction Y, and the ratio in number of pixels between the longitudinal direction W and the lateral direction Y is 18.4:1. A correction is performed in accordance with the ratio in number of pixels such that the width of the nonlinear image 31 in the lateral direction Y is expanded to 18.4 times the width before the correction in accordance with the ratio in number of pixels between the longitudinal direction and the lateral direction. A corrected image 31' obtained by such a correction is shown in FIG. 3B. It is possible to prevent a reduction in number of pixels by maintaining the width in the longitudinal direction W with a larger number of pixels, by expanding the width in the lateral direction while maintaining the width in the longitudinal direction W. Therefore, the accuracy of image processing can be maintained at an accuracy determined by the number of pixels in the longitudinal direction.

Thereafter, the angle of the corrected image 31' with the corrected aspect ratio of the frame is corrected in accordance with the refraction angle θb which is 48.8 degrees as described above. In this process, only the longitudinal direction W of the corrected image 31' is tilted by the refraction angle θb which is 48.8 degrees while keeping the lateral direction Y of the corrected image 31' in the horizontal direction. Consequently, the corrected image 31' is converted so as to conform to a parallelogram frame with the longitudinal direction X after the conversion corresponding to the vertical direction to obtain a frame conversion image 32a shown in FIG. 3C.

In the same manner as the case where the incident angle θa is +20 degrees, nonlinear images (not shown) for the other incident angles θa are also subjected to the image conversion process in which the frame aspect ratio is corrected and the angle is corrected in accordance with the refraction angle θb, so that the nonlinear images are converted so as to conform to a frame form matching the cross-sectional shape of the welded portion 23 of the exploration-target metal body 20 to generate frame conversion images 32a to 32h for each incident angle θa shown in FIGS. 4 and 5.

When the frame conversion images 32a to 32h for each incident angle θa are obtained as described above, the control processing device 9 performs the exploration image generation process described above. In this process, the frame conversion images 32a to 32h are subjected to a fast Fourier transform, and thereafter any two of the frame conversion images (32a to 32h) are selected to multiply echo signals 41 at the same coordinate position in the two frame conversion images. The thus calculated product is a value obtained by multiplying the intensities of the two echo signals 41. The multiplication process mentioned above is performed for all combinations of the echo signals 41. Then, each of the thus calculated products is determined in accordance with the predetermined signal intensity threshold for removing echo signals 41 generated by an orientation defect to remove all echo signals forming a product less than the signal intensity threshold from the two of the frame conversion images (32a to 32h). The frame conversion images (not shown) after this process are formed by only echo signals 41a for which the product is the signal intensity threshold or more. The process in which any two of the frame conversion images (32a to 32h) are selected to remove echo signals 41 for which the product is less than the signal intensity threshold as described above is executed for all combinations of the frame conversion images (32a to 32h) to generate a frame conversion image (not shown) formed by only echo signals 41a for which the product is the signal intensity threshold or more.

Thereafter, the size of all the frame conversion images formed by only the echo signals 41a is corrected so as to form the same frame size. In this process, the frame size of frame conversion images (not shown) other than a frame conversion image at an incident angle θa of +20 degrees (not shown), which has the largest number of pixels in the ultrasonic wave propagation direction, is adjusted to the frame size of the frame conversion image at an incident angle θa of +20 degrees. That is, the frame size of a frame conversion image other than the frame conversion image at an incident angle θa of +20 degrees is increased in accordance with the ratio between the number of pixels in the ultrasonic wave propagation direction in the frame conversion image at an incident angle θa of +20 degrees and the number of pixels in the ultrasonic wave propagation direction in that frame conversion image. For example, the number of pixels in the ultrasonic wave propagation direction is 184 in the case where the incident angle θa is +20 degrees, and the number of pixels in the ultrasonic wave propagation direction is 152 in the case where the incident angle θa is 16 degrees. Thus, the frame size of a frame conversion image with an incident angle θa of 16 degrees (not shown) is multiplied by "184/152".

After the frame size of the frame conversion images (not shown) is adjusted as described above, the frame conversion images are overlapped to obtain a nonlinear exploration image 35 shown in FIG. 6A as a cross-sectional image of the welded portion 23 of the exploration-target metal body 20. A cross-sectional photograph obtained by cutting the exploration-target metal body 20 along the direction in which the probe 4 is changed in position is shown in FIG. 6B. When the cross-sectional photograph and the nonlinear exploration image 35 generated by the ultrasonic exploration apparatus 1 according to the embodiment are compared, it can be seen that the nonlinear exploration image 35 shows the interface shape of the welded portion 23 accurately and clearly. That is, non-destructive inspection may be performed to accurately explore the interface shape of the welded portion 23 by generating the nonlinear exploration image 35 using the ultrasonic exploration apparatus 1 according to the embodiment. Thus, according to the ultrasonic exploration apparatus 1 of the embodiment, it is possible to stably provide the nonlinear exploration image 35 which shows the interface shape of the welded portion 23 accurately and clearly.

FIG. 9A shows a comparative image 37 obtained by overlapping the frame conversion images 32a to 37h generated in the image conversion process without performing the removal process based on the signal intensity threshold described above. With the comparative image 37, it is difficult to discriminate the interface shape of the welded portion 23 compared to the cross-sectional photograph of FIG. 6B described above. Even if the comparative image 37 and the cross-sectional photograph (FIG. 6B) are overlapped for display, the interface shape of the welded portion 23 is still unclear as shown in FIG. 9B. This emphasizes the importance of the use of the signal intensity threshold for removing echo signals 41 generated by an orientation defect in the embodiment.

According to the ultrasonic exploration apparatus 1 of the embodiment described above, non-destructive inspection can be performed on a welded portion of an automobile wheel formed by welding a disc and a rim, for example. Since the automobile wheels are important safety components as described above, quality control of the welded portion of the automobile wheels is important. In this case, a water tank (not shown) in which an automobile wheel can be immersed in water is provided. Then, after the automobile wheel is set in the water tank, the probe 4 drives the probe scanning device 11 so as to move in parallel to the wheel axis direction in order to perform the exploration operation described above. In the automobile wheel, the welded portion is formed at a plurality of locations. Therefore, an exploration operation may be performed at each of the locations to obtain a nonlinear exploration image. Then, by performing quality control of the welded portion using the nonlinear exploration images, it is possible to easily and accurately determine whether or not welding is performed normally at the welded portion.

In the embodiment configured as described above, in the exploration image generation process executed by the control processing device, echo signals at the same coordinate position in any two of the frame conversion images that have been subjected to a fast Fourier transform are multiplied to perform a determination using the signal intensity threshold. However, other processing methods may also be used. For example, echo signals at the same coordinate position in any two of the frame conversion images that have been subjected to a fast Fourier transform may be added to determine the resulting sum using a predetermined signal intensity threshold. Alternatively, echo signals at the same coordinate position in any two of frame conversion images that have been subjected to a Fourier transform or a maximum entropy method rather than a fast Fourier transform, may be multiplied or added to determine the resulting product or sum using a signal intensity threshold. Still alternatively, each echo signal may be determined using a predetermined signal intensity threshold for each frame conversion image that has been subjected to a fast Fourier transform. Likewise, each echo signal may be determined using a predetermined signal intensity threshold for each frame conversion image that has been subjected to a Fourier transform or a maximum entropy method rather than a fast Fourier transform. Whichever process is used, it is necessary to determine an appropriate signal intensity threshold for removing echo signal generated by an orientation defect.

In the embodiment described above, in the exploration image generation process, frame conversion images formed by echo signals whose signal intensity is the signal intensity threshold or more are generated, and then the frame size of each frame conversion image is changed. Alternatively, the frame size of each frame conversion image generated in the image conversion process may be changed, and then frame conversion images formed by echo signals whose signal intensity is the signal intensity threshold or more may be generated.

In the embodiment described above, steel plates are welded to each other for use as an exploration-target metal body. However, other metal materials may be welded to each other for use as an exploration-target metal body to explore the welded portion. In the case of an exploration-target metal body formed from other metal materials, the sonic speed of ultrasonic waves that propagate in the metal body is different, and thus it is necessary to measure the sonic speed in advance. Also, vertical waves and horizontal waves may occur at different incident angles among metal materials, and thus it is necessary to appropriately set the incident angle. For example, in the case where an exploration-target metal body obtained by welding aluminum alloys to each other is to be inspected, the incident angle of ultrasonic waves is appropriately set in a range of 0 degrees to ±8 degrees and a range of ±17 degrees to ±28 degrees. In a range in which the incident angle is more than ±8 degrees and less than ±17 degrees, the reflected waves contain vertical waves and horizontal waves mixed with each other, which hinders adequate inspection. In a range in which the incident angle exceeds ±28 degrees, the ultrasonic waves do not enter into the exploration-target metal body, which hinders inspection. It is further necessary to actually measure the sonic speed of vertical waves and horizontal waves of ultrasonic waves that propagate in the exploration-target metal body.

In the embodiment described above, the ultrasonic exploration apparatus 1 is used to explore a welded portion at which two steel plates are welded. However, the ultrasonic exploration apparatus 1 may be used for other purposes. For example, the ultrasonic exploration apparatus 1 may be used for inspecting the hardening depth of a hardened steel material. Specifically, in the case where an austenitic stainless steel is not hardened sufficiently, the austenitic stainless steel contains a martensitic structure generated by the hardening and an austenitic structure left unhardened. The crystal structure of the martensitic structure is a body-centered cubic lattice, and the crystal structure of the austenitic structure is face-centered cubic lattice. Thus, according to the ultrasonic exploration apparatus 1 of the embodiment, it is possible to acquire echo signals from harmonic waves containing interface-reflected waves reflected by the interface between the structures, thereby providing a nonlinear exploration image showing the interface shape. Also in the case, echo signals generated by an orientation defect in each structure are acquired. However, it is possible to show the interface shape accurately and clearly by removing echo signals whose signal intensity is a signal intensity threshold for removing echo signals or less.

The present invention is not limited to the embodiment described above, and may be modified appropriately within the scope and spirit of the present invention.

Description Of Reference Numerals And Symbols

1: ultrasonic exploration apparatus
4: probe
4a: transmission section
4b: reception section
5: high-frequency generator (ultrasonic wave generation means)
6: amplifier (ultrasonic wave generation means)
9: control processing device (scanning control means, exploration image processing means)
11: probe scanning device (probe scanning means)
12: probe scanning device (probe scanning means)
20: exploration-target metal body
23: welded portion (exploration-target area)
31: nonlinear image (for incident angle θa of +20 degrees)
32a to 32h: frame conversion image
35: nonlinear exploration image
41, 41a: echo signal
p: transmission/reception position
t: pitch distance
θa: incident angle
θb: refraction angle

The invention claimed is:

1. An ultrasonic exploration method configured to execute:
an exploration process for executing an exploration operation, in which a transmission/reception position, at which ultrasonic waves at a specified frequency are transmitted to an exploration-target area of an exploration-target metal body and reflected waves of the ultrasonic waves are received, is sequentially changed by a specified pitch distance, for each of a plurality of preset incident angles of the ultrasonic waves, extracting harmonic waves contained in the reflected waves for each of the incident angles, and generating for each of the incident angles a nonlinear image of the exploration-target area in which echo signals acquired from the harmonic waves are presented on the basis of a response time from transmission of the ultrasonic waves to reception of the reflected waves;
an image conversion process for converting the nonlinear image for each of the incident angles so as to conform to a frame form matching a cross-sectional shape of the exploration-target area on the basis of a refraction angle, at which the ultrasonic waves transmitted at the incident angle propagate in the exploration-target metal body, and the number of data prescribed in accordance with the refraction angle and a sonic speed of the ultrasonic waves to generate a frame conversion image for each of the incident angles; and
an exploration image generation process for determining in advance a signal intensity threshold for removing echo signals resulting from an orientation defect due to a mismatched crystal orientation in a crystal structure of the exploration-target metal body, and overlapping frame conversion images formed by only echo signals whose signal intensity is the signal intensity threshold or more to generate a nonlinear exploration image of the exploration-target area.

2. The ultrasonic exploration method according to claim 1, wherein the image conversion process includes correcting, for each of the nonlinear images at each of the incident angles, an aspect ratio of a frame in which the nonlinear image is presented on the basis of the number of data prescribed in accordance with the pitch distance of the transmission/reception position of the ultrasonic waves and the number of data prescribed in accordance with the refraction angle and the sonic speed of the ultrasonic waves, and thereafter correcting an angle of each of the nonlinear images at each of the incident angles, in addition to the cross-sectional shape of the exploration-target area, in accordance with the refraction angle to generate a frame conversion image for each of the incident angles.

3. The ultrasonic exploration method according to claim 2, wherein the exploration image generation process includes, before overlapping the frame conversion images, correcting a size of frame conversion images other than a frame conversion image with the largest number of data so as to match the frame conversion images in frame size with the frame conversion image with the largest number of data.

4. An ultrasonic exploration apparatus comprising:
ultrasonic wave generation means for generating ultrasonic waves at a specified frequency;
a probe including a transmission section that transmits the ultrasonic waves generated by the ultrasonic wave generation means and a reception section that receives reflected waves of the ultrasonic waves;
probe scanning means for moving the probe so as to vary a transmission/reception position at which the ultrasonic waves are transmitted and the reflected waves are received;
probe tilting means for tilting the probe so as to adjust an incident angle at which the ultrasonic waves are incident on an exploration-target metal body;
scanning control means for performing an exploration operation, in which the transmission/reception position is sequentially changed by a specified pitch distance while holding the probe at a specified incident angle, for each of a plurality of preset incident angles by controlling operation of the probe scanning means and the probe tilting means; and
exploration image processing means including:
an image generation process content for extracting from the reflected waves received by the probe harmonic waves contained in the reflected waves for each of the incident angles to generate for each of the incident angles a nonlinear image in which echo signals acquired from the harmonic waves are presented on the basis of a response time from transmission of the ultrasonic waves to reception of the reflected waves;
an image conversion process content for converting the nonlinear image for each of the incident angles so as to conform to a frame form matching a cross-sectional shape of the exploration-target metal body on the basis of a refraction angle, at which the ultrasonic waves transmitted at the incident angle propagate in the exploration-target metal body, and the number of data prescribed in accordance with the refraction angle and a sonic speed of the ultrasonic waves to generate a frame conversion image for each of the incident angles; and an exploration image generation process content for determining in advance a signal intensity threshold for removing echo signals resulting from an orientation defect due to a mismatched crystal orientation in a crystal structure of the exploration-target metal body, and overlapping frame conversion images formed by only echo signals whose signal intensity is the signal intensity threshold or more to generate a nonlinear exploration image of the exploration-target area.

* * * * *